United States Patent [19]
Norris et al.

[11] Patent Number: 5,576,294
[45] Date of Patent: Nov. 19, 1996

[54] HUMAN KUNITZ-TYPE PROTEASE INHIBITOR VARIANT

[75] Inventors: Fanny Norris; Kjeld Norris, both of Hellerup; Søren E. Bjørn, Lyngby; Lars C. Petersen, Hørsholm; Ole H. Olsen, Brønshøj, all of Denmark

[73] Assignee: Novo Nordisk A/S, Bagsvaerd, Denmark

[21] Appl. No.: 321,658

[22] Filed: Oct. 12, 1994

Related U.S. Application Data

[63] Continuation of Ser. No. 21,610, filed as PCT/DK93/00004, Jan. 7, 1993, abandoned.

[30] Foreign Application Priority Data

Jan. 7, 1992 [WO] WIPO ............... PCT/DK92/00001

[51] Int. Cl.$^6$ .................. A61K 38/00; C12P 21/06; C07K 1/00; C07H 19/00
[52] U.S. Cl. .................. 514/12; 435/69.1; 435/189; 435/240.2; 435/320.1; 514/2; 530/350; 536/22.1; 536/23.1; 536/23.2; 536/23.5
[58] Field of Search ............... 435/69.1, 189, 435/240.2, 320.1; 514/2, 12; 536/22.1, 23.1, 23.2, 23.5; 530/350

[56] References Cited

U.S. PATENT DOCUMENTS 5,106,833 4/1993 Broze, Jr. et al. ............... 514/12

OTHER PUBLICATIONS

Girard et al., "Functional significance...", Nature, vol. 338, pp. 518–520, Apr. 6, 1989.
Glover, "Recombination and mutagenesis", Gene Cloning, pp. 21–45, 1984.

Primary Examiner—Robert A. Wax
Assistant Examiner—Hyosuk Kim
Attorney, Agent, or Firm—Steve T. Zelson; Elias J. Lambiris

[57] ABSTRACT

Variant of human Kunitz-type protease inhibitor domain II of tissue factor pathway inhibitor (TFPI), the variant comprising the following amino acid sequence Xaa Xaa Xaa Xaa Xaa Asp Phe Cys Phe Leu Glu Glu Asp Xaa
 1            5                     10

Gly Xaa Cys Xaa Xaa Xaa Xaa Xaa Xaa Tyr Phe Tyr Asn Asn
15           20              25

Gln Thr Lys Gln Cys Glu Arg Phe Xaa Tyr Gly Gly Cys Xaa
       30              35              40

Xaa Xaa Met Asn Asn Phe Xaa Thr Leu Glu Glu Cys Lys Asn
     45              50                  55

Ile Cys Glu Asp Xaa Xaa Xaa Xaa Xaa (SEQ ID NO:1)
        60              65 wherein Xaa at position 1 is H or a naturally occurring amino acid residue except Cys, each Xaa at positions 2–5 is independently a naturally occurring amino acid residue except Cys or is absent, each Xaa at positions 14, 16, 18, 19, 20, 21, 22, 23, 37, 42, 43, 44, and 49 independently a naturally occurring amino acid except Cys, each Xaa at positions 61, 62, 63, and 64 is independently a naturally occurring amino acid except Cys or is absent, and Xaa at position 65 is OH or a naturally occurring amino acid except Cys, with the proviso that at least one of the amino acid residues designated Xaa is different from the amino acid residue of the native sequence.

12 Claims, 3 Drawing Sheets

GLANDULAR KALLIKREIN

PLASMA KALLIKREIN

CATHEPSIN G

NEUTROPHIL ELASTASE

HUMAN KUNITZ-TYPE PROTEASE INHIBITOR VARIANT

CROSS-REFERENCE TO RELATED APPLICATIONS

This application is a continuation of application Ser. No. 08/021,610, filed Feb. 22, 1993, now abandoned, which is a continuation of international application PCT/DK93/00004, filed Jan. 7, 1993, which are incorporated herein by reference.

FIELD OF INVENTION

The present invention relates to a variant of a human Kunitz-type protease inhibitor domain, DNA encoding the variant, a method of producing the variant and a pharmaceutical composition containing the variant.

BACKGROUND OF THE INVENTION

Polymorphonuclear leukocytes (neutrophils or PMNs) and mononuclear phagocytes (monocytes) play an important part in tissue injury, infection, acute and chronic inflammation and wound healing. The cells migrate from the blood to the site of inflammation and, following appropriate stimulation, they release oxidant compounds ($O_2 \cdot$, $O_2-$, $H_2O_2$ and HOCl) as well as granules containing a variety of proteolytic enzymes. The secretory granules contain, i.a., alkaline phosphatase, metalloproteinases such as gelatinase and collagenase and serine proteases such as neutrophil elastase, cathepsin G and proteinase 3.

Latent metalloproteinases are released together with tissue inhibitor of metalloproteinase (TIMP). The activation mechanism has not been fully elucidated, but it is likely that oxidation of thiol groups and/or proteolysis play a part in the process. Also, free metalloproteinase activity is dependent on inactivation of TIMP.

In the azurophil granules of the leukocytes, the serine proteases neutrophil elastase, cathepsin G and proteinase-3 are packed as active enzymes complexed with glucosaminoglycans. These complexes are inactive but dissociate on secretion to release the active enzymes. To neutralize the protease activity, large amounts of the inhibitors $\alpha_1$-proteinase inhibitor ($\alpha_1$-PI) and $\alpha_1$-chymotrypsin inhibitor ($\alpha_1$-ChI) are found in plasma. However, the PMNs are able to inactivate the inhibitors locally. Thus, $\alpha_1$-PI which is the most important inhibitor of neutrophil elastase is sensitive to oxidation at the reactive center (Met-358) by oxygen metabolites produced by triggered PMNs. This reduces the affinity of $\alpha_1$-PI for neutrophil elastase by approximately 2000 times.

After local neutralization of $\alpha_1$-PI, the elastase is able to degrade a number of inhibitors of other proteolytic enzymes. Elastase cleaves $\alpha_1$-ChI and thereby promotes cathepsin G activity. It also cleaves TIMP, resulting in tissue degradation by metalloproteinases. Furthermore, elastase cleaves antithrombin III and heparin cofactor II, and tissue factor pathway inhibitor (TFPI) which probably promotes clot formation. On the other hand, the ability of neutrophil elastase to degrade coagulation factors is assumed to have the opposite effect so that the total effect of elastase is unclear. The effect of neutrophil elastase on fibrinolysis is less ambiguous. Fibrinolytic activity increases when the elastase cleaves the plasminogen activator inhibitor and the $\alpha_2$ plasmin inhibitor. Besides, both of these inhibitors are oxidated and inactivated by $O_2$ metabolites.

PMNs contain large quantities of serine proteases, and about 200 mg of each of the leukocyte proteases are released daily to deal with invasive agents in the body. Acute inflammation leads to a many-fold increase in the amount of enzyme released. Under normal conditions, proteolysis is kept at an acceptably low level by large amounts of the inhibitors $\alpha_1$-PI, $\alpha_1$-ChI and $\alpha_2$ macroglobulin. There is some indication, however, that a number of chronic diseases is caused by pathological proteolysis due to overstimulation of the PMNs, for instance caused by autoimmune response, chronic infection, tobacco smoke or other irritants, etc.

Aprotinin (bovine pancreatic trypsin inhibitor) is known to inhibit various serine proteases, including trypsin, chymotrypsin, plasmin and kallikrein, and is used therapeutically in the treatment of acute pancreatitis, various states of shock syndrome, hyperfibrinolytic hemorrhage and myocardial infarction (cf., for instance, J. E. Trapnell et al, *Brit. J. Surg.* 61, 1974, p. 177; J. McMichan et al., *Circulatory shock* 9, 1982, p. 107; L. M. Auer et al., *Acta Neurochir.* 49, 1979, p. 207; G. Sher, *Am. J. Obstet. Gynecol.* 129, 1977, p. 164; and B. Schneider, *Artzneim.-Forsch.* 26, 1976, p. 1606). Administration of aprotinin in high doses significantly reduces blood loss in connection with cardiac surgery, including cardiopulmonary bypass operations (cf., for instance, B. P. Bidstrup et al., *J. Thorac. Cardiovasc. Surg.* 97, 1989, pp. 364–372; W. van Oeveren et al., *Ann. Thorac. Surg.* 44, 1987, pp. 640–645). It has previously been demonstrated (cf. H. R. Wenzel and H. Tschesche, *Angew. Chem. Internat. Ed.* 20, 1981, p. 295) that certain aprotinin analogues, e.g. aprotinin(1-58, Val15) exhibits a relatively high selectivity for granulocyte elastase and an inhibitory effect on collagenase, aprotinin (1-58, Ala15) has a weak effect on elastase, while aprotinin (3-58, Arg15, Ala17, Ser42) exhibits an excellent plasma kallikrein inhibitory effect (cf. WO 89/10374).

However, when administered in vivo, aprotinin has been found to have a nephrotoxic effect in rats, rabbits and dogs after repeated injections of relatively high doses of aprotinin (Bayer, *Trasylol, Inhibitor of proteinase;* E. Glaser et al. in "Verhandlungen der Deutschen Gesellschaft für Innere Medizin, 78. Kongress", Bergmann, München, 1972, pp. 1612–1614). The nephrotoxicity (i.a. appearing in the form of lesions) observed for aprotinin might be ascribed to the accumulation of aprotinin in the proximal tubulus cells of the kidneys as a result of the high positive net charge of aprotinin which causes it to be bound to the negatively charged surfaces of the tubuli. This nephrotoxicity makes aprotinin less suitable for clinical purposes, in particular those requiring administration of large doses of the inhibitor (such as cardiopulmonary bypass operations). Besides, aprotinin is a bovine protein which may therefore contain one or more epitopes which may give rise to an undesirable immune response on administration of aprotinin to humans.

It is therefore an object of the present invention to identify human protease inhibitors of the same type as aprotinin (i.e. Kunitz-type inhibitors) with a similar inhibitor profile or modified to exhibit a desired inhibitor profile.

SUMMARY OF THE INVENTION

The present invention relates to a variant of human Kunitz-type protease inhibitor domain II of tissue factor pathway inhibitor (TFPI), the variant comprising the following amino acid sequence Xaa Xaa Xaa Xaa Xaa Asp Phe Cys Phe Leu Glu Glu Asp Xaa
1           5                    10

Gly Xaa Cys Xaa Xaa Xaa Xaa Xaa Tyr Phe Tyr Asn Asn
15              20                  25

Gln Thr Lys Gln Cys Glu Arg Phe Xaa Tyr Gly Gly Cys Xaa
    30              35                  40

Xaa Xaa Met Asn Asn Phe Xaa Thr Leu Glu Glu Cys Lys Asn
       45                50                  55

Ile Cys Glu Asp Xaa Xaa Xaa Xaa Xaa (SEQ ID NO:1)
            60                  65 wherein Xaa at position 1 is H or a naturally occurring amino acid residue except Cys, each Xaa at positions 2–5 is independently a naturally occurring amino acid residue except Cys or is absent, each Xaa at positions 14, 16, 18, 19, 20, 21, 22, 23, 37, 42, 43, 44, and 49 independently a naturally occurring amino acid except Cys, each Xaa at positions 61, 62, 63, and 64 is independently a naturally occurring amino acid except Cys or is absent, and Xaa at position 65 is OH or a naturally occurring amino acid except Cys, with the proviso that at least one of the amino acid residues designated Xaa is different from the amino acid residue of the native sequence.

In the present context, the term "naturally occurring amino acid residue" is intended to indicate any one of the 20 commonly occurring amino acids, i.e. Ala, Val, Leu, Ile Pro, Phe, Trp, Met, Gly, Ser, Thr, Cys, Tyr, Asn, Gln, Asp, Glu, Lys, Arg and His.

TFPI, also known as extrinsic pathway inhibitor (EPI) or lipoprotein associated coagulation inhibitor (LACI), has been isolated by Broze et al. (*Proc. Natl. Acad. Sci. U.S.A.* 84, 1987, pp. 1886–1890 and EP 300 988) and the gene coding for the protein has been cloned, cf. EP 318 451. Analysis of the secondary structure of the protein has shown that the protein has three Kunitz-type inhibitor domains, from amino acid 22 to amino acid 79 (I), from amino acid 93 to amino acid 150 (II) and from amino acid 185 to amino acid 242 (III). Kunitz-type domain I of TFPI has been shown to bind TF/FVIIa, while Kunitz-type domain II has been shown to bind to FXa (Girard et al., *Nature* 338, 1989, pp. 518–520).

By substituting one or more amino acids in one or more of the positions indicated above, it may be possible to change the inhibitor profile of TFPI Kunitz-type domain II so that it preferentially inhibits neutrophil elastase, cathepsin G and/or proteinase-3. Furthermore, it may be possible to construct variants which specifically inhibit enzymes involved in coagulation or fibrinolysis (e.g. plasmin or plasma kallikrein) or the complement cascade.

One advantage of TFPI Kunitz-type domain II is that it has a negative net charge as opposed to aprotinin which, as indicated above, has a strongly positive net charge. It is therefore possible to construct variants of the invention with a lower positive net charge than aprotinin, thereby reducing the risk of kidney damage on administration of large doses of the variants. Another advantage is that, contrary to aprotinin, it is a human protein (fragment) so that undesired immunological reactions on administration to humans are significantly reduced.

DETAILED DISCLOSURE OF THE INVENTION

Figure 1:
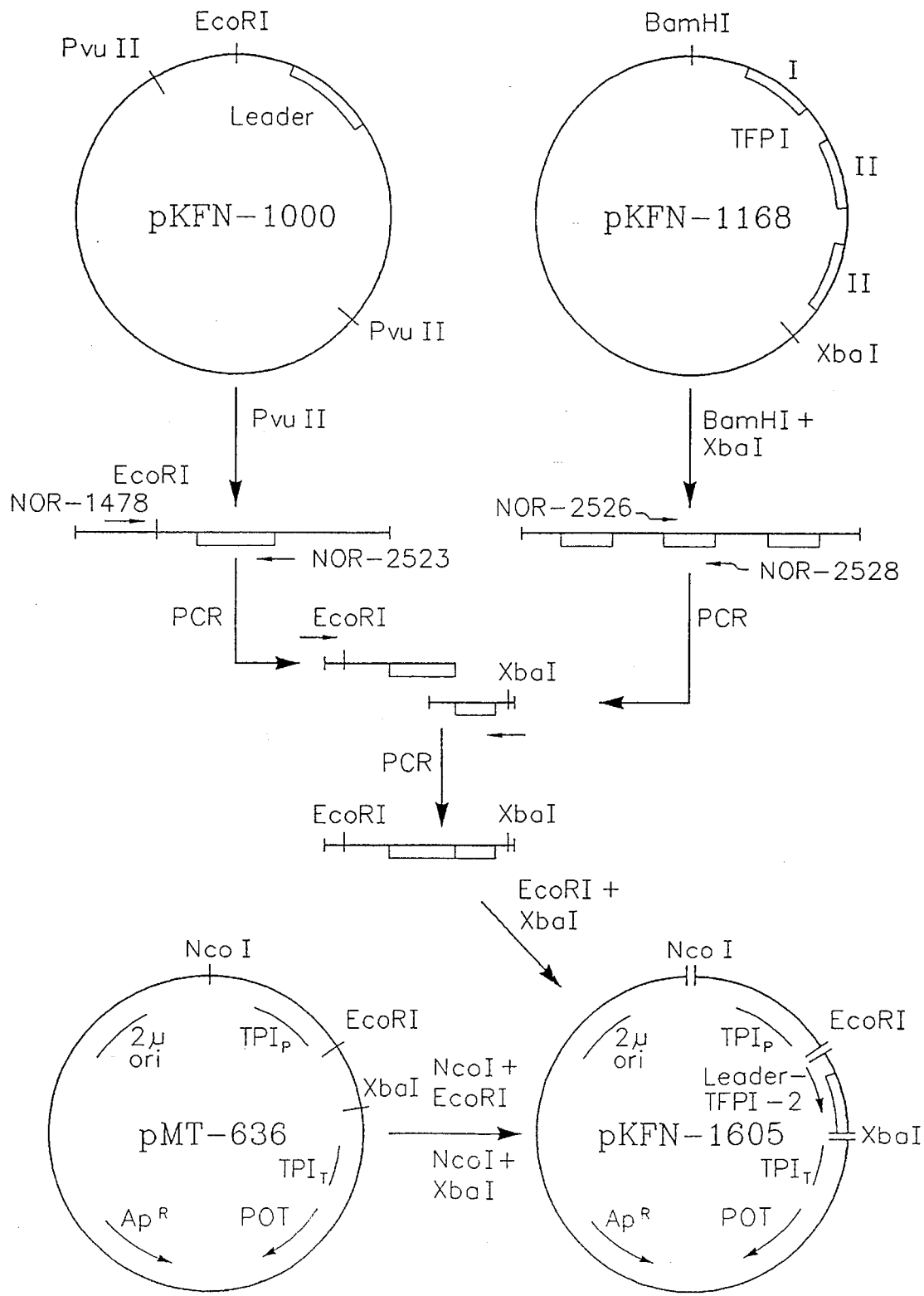
FIG. 1 shows the construction of pKPN-1605.

Examples of preferred variants(all positions referring to numbering of SEQ ID NO:1) of Kunitz-type domain II of TFPI are variants wherein Xaa at position 1 and Xaa at position 2 are, respectively, Lys and Pro, and Xaa at positions 3, 4 and 5 are absent; or wherein Xaa at position 14 is an amino acid residue selected from the group consisting of Ala, Arg, Thr, Asp, Pro, Glu, Lys, Gln, Ser, Ile and Val, in particular wherein this Xaa is Thr or Pro; or wherein Xaa at position 16 is an amino acid residue selected from the group consisting of Pro, Thr, Leu, Arg, Val and Ile, in particular wherein this Xaa is Pro or Ile; or wherein the Xaa at position 18 is an amino acid residue selected from the group consisting of Lys, Arg, Val, Thr, Ile, Leu, Phe, Gly, Ser, Met, Trp, Tyr, Gln, Asn and Ala, in particular wherein this Xaa is Lys, Val, Leu, Ile, Thr, Met, Gln or Arg; or wherein Xaa at position 19 is an amino acid residue selected from the group consisting of Ala, Gly, Thr, Arg, Phe, Gln and Asp, in particular wherein this Xaa is Ala, Thr, Asp or Gly; or wherein Xaa at position 20 is an amino acid residue selected from the group consisting of Arg, Ala, Lys, Leu, Gly, His, Ser, Asp, Gln, Glu, Val, Thr, Tyr, Phe, Asn, Ile and Met, in particular wherein this Xaa is Arg, Phe, Ala, Leu or Tyr; or wherein Xaa at position 21 is an amino acid residue selected from the group consisting of Ile, Met, Gln, Glu, Thr, Leu, Val and Phe, in particular wherein this Xaa is Ile; or wherein Xaa at position 22 is an amino acid residue selected from the group consisting of Ile, Thr, Leu, Asn, Lys, Ser, Gln, Glu, Arg, Pro and Phe, in particular wherein this Xaa is Ile or Thr; or wherein Xaa at position 23 is an amino acid residue selected from the group consisting of Arg, Ser, Ala, Gln, Lys and Leu, in particular wherein this Xaa is Arg; or wherein Xaa at position 37 is an amino acid residue selected from the group consisting of Gln, Pro, Phe, Ile Lys, Trp, Ala, Thr, Leu, Ser, Tyr, His, Asp, Met, Arg and Val, in particular wherein this Xaa is Val or Lys; or wherein Xaa at position 42 is an amino acid residue selected from the group consisting of Gly, Met, Gln, Glu, Leu, Arg, Lys, Pro and Asn, in particular wherein this Xaa is Arg or Leu; or wherein Xaa at position 43 is Ala or Gly; or wherein Xaa at position 44 is an amino acid residue selected from the group consisting of Lys, Asn and Asp, in particular wherein $X^{13}$ is Lys or Asn; or wherein $X^{14}$ is an amino acid residue selected from the group consisting of Val, Tyr, Asp, Glu, Thr, Gly, Leu, Ser, Ile, Gln, His, Asn, Pro, Phe, Met, Ala, Arg, Trp and Lys, in particular wherein this Xaa is Lys or Glu; or wherein Xaa at position 49 is Gly. In a preferred embodiment, Xaa at positions 1 and 2 are, respectively, Lys and Pro and Xaa at position 49 is Gly, while the remaining Xaa's are as defined above.

Variants of TFPI Kunitz-type domain II of the invention should preferably not contain a Met residue in the protease binding region (i.e. the amino acid residues represented by positions 16, 18, 19, 20, 21, 22, 23, 37, 42, 43, 44, and 49). By analogy to α1-PI described above, a Met residue in any one of these positions would make the inhibitor sensitive to oxidative inactivation by oxygen metabolites produced by PMNs, and conversely, lack of a Met residue in these positions should render the inhibitor more stable in the presence of such oxygen metabolites.

It may be desired to change the way in which the TFPI Kunitz-type domain II variant is glycosylated when produced by a host cell. Thus, in one embodiment, the variant of the invention may have the following amino acid sequence (SEQ ID NO: 2)
Xaa Xaa Xaa Xaa Xaa Asp Phe Cys Phe Leu Glu Glu Asp Xaa
1             5                  10

Gly Xaa Cys Xaa Xaa Xaa Xaa Xaa Tyr Phe Tyr Asn Xaa Gln
15              20                  25

Xaa Lys Gln Cys Glu Arg Phe Xaa Tyr Gly Gly Cys Xaa Xaa Xaa
30              35                  40

Met Asn Asn Phe Xaa Thr Leu Glu Glu Cys Lys Asn Ile Cys Glu
45              50                  55

Asp Xaa Xaa Xaa Xaa
60          65 wherein the Xaa's at positions 16, 18, 19, 20, 21, 22, 23, 37, 42, 43, 44, 49, 61, 62, 63, 64 and 65 are as specified in SEQ ID NO:1, Xaa at position 28 selected from the group consisting of Gln, Gly, Ala, Ser, Val and Phe, in particular Gln or Ala, and Xaa at position 30 is an amino acid residue selected from the group consisting of Thr or Ala.

Currently preferred variants of the invention are those in which one or more the amino acid residues located at the protease-binding site of the Kunitz domain (i.e. one or more of the Xaa's at positions 16, 18, 19, 20, 21, 22, 23, 37, 42, 43, 44, and 49 of SEQ ID NO: 1, corresponding to positions 13, 15, 16, 17, 18, 19, 20, 34, 39, 40, 41 and 46 of aprotinin) are substituted to the amino acids present in the same position(s) of native aprotinin.

Examples of such variants are Lys Pro Asp Phe Cys Phe Leu Glu Glu Asp Pro Gly Ile Cys Lys Ala Arg Ile Thr Arg Tyr Phe Tyr Asn Asn Gln Thr Lys Gln Cys Glu Arg Phe Lys Tyr Gly Gly Cys Leu Gly Asn Met Asn Asn Phe Glu Thr Leu Glu Glu Cys Lys Asn Ile Cys Glu Asp Gly (SEQ ID No. 3);

Lys Pro Asp Phe Cys Phe Leu Glu Glu Asp Pro Gly Ile Cys Lys Ala Arg Ile Thr Arg Tyr Phe Tyr Asn Asn Gln Thr Lys Gln Cys Glu Arg Phe Lys Tyr Gly Gly Cys Arg Gly Asn Met Asn Asn Phe Glu Thr Leu Glu Glu Cys Lys Asn Ile Cys Glu Asp Gly (SEQ ID No. 4);

Lys Pro Asp Phe Cys Phe Leu Glu Glu Asp Pro Gly Ile Cys Lys Ala Arg Ile Thr Arg Tyr Phe Tyr Asn Asn Gln Thr Lys Gln Cys Glu Arg Phe Lys Tyr Gly Gly Cys Arg Gly Asn Met Asn Asn Phe Lys Thr Leu Glu Glu Cys Lys Asn Ile Cys Glu Asp Gly (SEQ ID No. 5); or

Lys Pro Asp Phe Cys Phe Leu Glu Glu Asp Pro Gly Pro Cys Lys Ala Arg Ile Ile Arg Tyr Phe Tyr Asn Asn Gln Thr Lys Gln Cys Glu Arg Phe Val Tyr Gly Gly Cys Arg Ala Lys Met Asn Asn Phe Lys Thr Leu Glu Glu Cys Lys Asn Ile Cys Glu Asp Gly (SEQ ID No. 6).

In another aspect, the invention relates to a DNA construct encoding a human Kunitz-type inhibitor domain variant according to the invention. The DNA construct of the invention may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

Alternatively, it is possible to use genomic or cDNA coding for TFPI Kunitz-type domain II (e.g. obtained by screening a genomic or cDNA library for DNA coding for TFPI using synthetic oligonucleotide probes and isolating the DNA sequence coding for domain II therefrom). The DNA sequence is modified at one or more sites corresponding to the site(s) at which it is desired to introduce amino acid substitutions, e.g. by site-directed mutagenesis using synthetic oligonucleotides encoding the desired amino acid sequence for homologous recombination in accordance with well-known procedures.

In a still further aspect, the invention relates to a recombinant expression vector which comprises a DNA construct of the invention. The recombinant expression vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the TFPI Kunitz-type domain II variant of the invention should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the TFPI Kunitz-type domain II variant of the invention in mammalian cells are the SV 40 promoter (Subramani et al., *Mol. Cell Biol.* 1, 1981, pp. 854–864), the MT-1 (metallothionein gene) promoter (Palmiter et al., *Science* 222, 1983, pp. 809–814) or the adenovirus 2 major late promoter. Suitable promoters for use in yeast host cells include promoters from yeast glycolytic genes (Hitzeman et al., *J. Biol. Chem.* 255, 1980, pp. 12073–12080; Alber and Kawasaki, *J. Mol. Appl. Gen.* 1, 1982, pp. 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304, 1983, pp. 652–654) promoters. Suitable promoters for use in filamentous fungus host cells are, for instance, the ADH3 promoter (McKnight et al., *The EMBO J.* 4, 1985, pp. 2093–2099) or the tpiA promoter.

The DNA sequence encoding the TFPI Kunitz-type domain II variant of the invention may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector of the invention may further comprise a DNA sequence enabling the vector to replicate in the host cell in question. An example of such a sequence (when the host cell is a mammalian cell) is the SV 40 origin of replication, or (when the host cell is a yeast cell) the yeast plasmid 2μ replication genes REP 1–3 and origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate, or the *Schizosaccharomyces pombe* TPI gene (described by P. R. Russell, *Gene* 40, 1985, pp. 125–130.

The procedures used to ligate the DNA sequences coding for the TFPI Kunitz-type domain II variant of the invention, the promoter and the terminator, respectively, and to insert them into suitable vectors containing the information necessary for replication, are well known to persons skilled in the art (cf., for instance, Sambrook et al., *Molecular Cloning: A Laboratory Manual,* Cold Spring Harbor, N.Y., 1989).

The host cell into which the expression vector of the invention is introduced may be any cell which is capable of producing the TFPI Kunitz-type domain II variant of the invention and is preferably a eukaryotic cell, such as a mammalian, yeast or fungal cell.

The yeast organism used as the host cell according to the invention may be any yeast organism which, on cultivation, produces large quantities of the TFPI Kunitz-type domain II variant of the invention. Examples of suitable yeast organisms are strains of the yeast species *Saccharomyces cerevisiae, Saccharomyces kluyveri, Schizosaccharomyces pombe* or *Saccharomyces uvarum.* The transformation of yeast cells may for instance be effected by protoplast formation followed by transformation in a manner known per se.

Examples of suitable mammalian cell lines are the COS (ATCC CRL 1650), BHK (ATCC CRL 1632, ATCC CCL 10) or CHO (ATCC CCL 61) cell lines. Methods of transfecting mammalian cells and expressing DNA sequences introduced in the cells are described in e.g. Kaufman and Sharp, *J. Mol. Biol.* 159, 1982, pp. 601–621; Southern and Berg, *J. Mol. Appl. Genet.* 1, 1982, pp. 327–341; Loyter et al., *Proc. Natl. Acad. Sci. U.S.A.* 79, 1982, pp. 422–426; Wigler et al., *Cell* 14, 1978, p. 725; Corsaro and Pearson, *Somatic Cell Genetics* 7, 1981, p. 603, Graham and van der Eb, *Virology* 52, 1973, p. 456; and Neumann et al., *EMBO J.* 1, 1982, pp. 841–845.

Alternatively, fungal cells may be used as host cells of the invention. Examples of suitable fungal cells are cells of filamentous fungi, e.g. *Aspergillus* spp. or *Neurospora* spp., in particular strains of *Aspergillus oryzae* or *Aspergillus niger.* The use of *Aspergillus* spp. for the expression of proteins is described in, e.g., EP 238 023.

The present invention further relates to a method of producing a TFPI Kunitz-type domain II variant according to the invention, the method comprising culturing a cell as described above under conditions conducive to the expression of the variant and recovering the resulting variant from the culture.

The medium used to cultivate the cells may be any conventional medium suitable for growing mammalian cells or fungal (including yeast) cells, depending on the choice of host cell. The variant will be secreted by the host cells to the growth medium and may be recovered therefrom by conventional procedures including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like.

The present invention also relates to a pharmaceutical composition comprising a TFPI Kunitz-type domain II variant of the invention together with a pharmaceutically acceptable carrier or excipient. In the composition of the invention, the variant may be formulated by any of the established methods of formulating pharmaceutical compositions, e.g. as described in *Remington's Pharmaceutical Sciences,* 1985. The composition may typically be in a form suited for systemic injection or infusion and may, as such, be formulated with sterile water or an isotonic saline or glucose solution.

The TFPI Kunitz-type domain II variant of the invention is therefore contemplated to be advantageous to use for the therapeutic applications suggested for native aprotinin or aprotinin analogues with other inhibitor profiles, in particular those which necessitate the use of large aprotinin doses. Therapeutic applications for which the use of the variant of the invention is indicated as a result of its ability to inhibit human serine proteases, e.g. trypsin, plasmin, kallikrein, elastase, cathepsin G and proteinase-3, include (but are not limited to) acute pancreatitis, inflammation, thrombocytopenia, preservation of platelet function, organ preservation, wound healing, shock (including shock lung) and conditions involving hyperfibrinolytic hemorrhage, emphysema, rheumatoid arthritis, adult respiratory distress syndrome, chronic inflammatory bowel disease and psoriasis, in other words diseases presumed to be caused by pathological proteolysis by elastase, cathepsin G and proteinase-3 released from triggered PMNs.

Furthermore, the present invention relates to the use of TFPI Kunitz-type inhibitor domain II or a variant thereof as described above for the preparation of a medicament for the prevention or therapy of diseases or conditions associated with pathological proteolysis by proteases released from overstimulated PMNs. As indicated above, it may be an advantage of administer heparin concurrently with the TFPI Kunitz-type inhibitor domain II or variant.

Apart from the pharmaceutical use indicated above, TFPI Kunitz-type domain II or a variant thereof as specified above may be used to isolate useful natural substances, e.g. proteases or receptors from human material, which bind directly or indirectly to TFPI Kunitz-type domain II, for instance by screening assays or by affinity chromatography.

EXAMPLES

General Methods

Standard DNA techniques were carried out as described (Sambrook, J., Fritsch, E. F., and Maniatis, T. (1989) Molecular Cloning: A Laboratory Manual, Cold Spring Harbor Laboratory Press, Cold Spring Harbor, N.Y.). Synthetic oligonucleotides were prepared on an automatic DNA synthesizer (380B, Applied Biosystems) using phosphoramidite chemistry on a controlled pore glass support (Beaucage, S. L., and Caruthers, M. H., *Tetrahedron Letters* 22, (1981) 1859–1869). DNA sequence determinations were performed by the dideoxy chain-termination technique (Sanger, F., Micklen, S., and Coulson, A. R., Proc. Natl. Acad. Sci. U.S.A. 74 (1977) 5463–5467). Polymerase chain reactions (PCR) were performed on a DNA Thermal Cycler (Perkin Elmer Cetus).

Amino acid analysis was carried out after hydrolysis in 6M HCl at 110° C. in vacuum-sealed tubes for 24 hours. Analysis was performed on a Beckman 121MB automatic amino acid analyzer modified for microbore operation.

N-terminal amino acid sequence analysis was obtained by automated Edman degradation using an Applied Biosystems 470A gas-phase sequencer. Analysis by on-line reverse phase HPLC was performed for the detection and quantitation of the liberated PTH amino acids from each sequencer cycle.

Molecular weight determination was obtained on a BIO-ION 20 plasma desorption mass spectrometer (PDMS) equipped with a flight tube of approximately 15 cm and operated in positive mode. Aliquots of 5 µl were analyzed at an accelerating voltage set to 15 kV and ions were collected for 5 million fission events. The accuracy on assigned molecular ions is approximately 0.1% for well defined peaks, otherwise somewhat less.

EXAMPLE 1

Production of the Second Kunitz Domain of Tissue Factor Pathway Inhibitor, TFPI-2, from Yeast Strain KFN-1593 cDNA encoding full length TFPI was isolated from the human liver derived cell line HepG2 (ATCC HB 8065) and inserted as a 0.9 kb BamHI—XbaI fragment into a mammalian expression vector, pKFN-1168, as described (Pedersen, A. H., Nordfang, O., Norris, F., Wiberg, F. C., Christensen, P. M., Moeller, K. B., Meidahl-Pedersen, J., Beck, T. C., Norris, K., Hedner, U., and Kisiel, W. 1990, J. Biol. Chem. 265, 16786–16793). The DNA sequence of the insert is given in SEQ ID No. 7. TFPI-2 is encoded by nucleotides 365–538 as indicated.

TFPI-2: 0.1 µg of the 0.9 kb BamHI-XbaI fragment from pKFN-1168 was used as a template in a PCR reaction containing 100 pmole each of the primers NOR-2526 (GCT-GAGAGATTGGAGAAGAGAAAGCCA-GATTTCTGCTT) and NOR-2528 (CTGGAATCTAGAT-TAACCATCTTCACAAATGTT). The 17 3'-terminal bases of NOR-2526 are identical to bases 365 to 381 in the TFPI-2 gene in SEQ ID No. 7, and the 21 5'-terminal bases are identical to bases 215 to 235 in the synthetic leader gene (see FIG. 2) from pKFN-1000 described below. Primer NOR-2528 is complementary to bases 521 to 540 in SEQ ID No. 7 and has a 5' extension containing a translation stop codon followed by an XbaI site.

The PCR reaction was performed in a 100 µl volume using a commercial kit (GeneAmp, Perkin Elmer Cetus) and the following cycle: 94° for 20 sec, 50° for 20 sec, and 72° for 30 sec. After 19 cycles a final cycle was performed in which the 72° step was maintained for 10 min. The PCR product, a 210 bp fragment, was isolated by electrophoresis on a 2% agarose gel.

Signal-leader: 0.1 µg of a 0.7 kb PvuII fragment from pKFN-1000 described below was used as a template in a PCR reaction containing 100 pmole each of the primers NOR-1478 (GTAAAACGACGGCCAGT) and NOR-2523 (TCTCTTCTCCAATCTCTCAGC). NOR-1478 is matching a sequence just upstream of the EcoRI site in SEQ ID No. 9. Primer NOR-2523 is complementary to the 17 3'-terminal bases of the synthetic leader gene of pKFN-1000, see SEQ ID No. 9. The PCR reaction was performed as described above, resulting in a 257 bp fragment.

Plasmid pKFN-1000 is a derivative of plasmid pTZ19R (Mead, D. A., Szczesna-Skorupa, E. and Kemper, B., Prot. Engin. 1 (1986) 67–74) containing DNA encoding a synthetic yeast signal-leader peptide. Plasmid pKFN-1000 is described in WO 90/10075. The DNA sequence of 235 bp downstream from the EcoRI site of pKFN-1000 and the encoded amino acid sequence of the synthetic yeast signal-leader is given in SEQ ID No. 9.

Signal-leader-TFPI-2: Approx. 0.1 µg of each of the two PCR-fragments described above were mixed. A PCR reaction was performed using 100 pmole each of primers NOR-1478 and NOR-2528 and the following cycle: 94° for 1 min, 50° for 2 min, and 72° for 3 min. After 16 cycles a final cycle was performed in which the 72° step was maintained for 10 min.

The resulting 442 bp fragment was purified by electrophoresis on a 1% agarose gel and then digested with EcoRI and XbaI. The resulting 412 bp fragment was ligated to the 9.5 kb NcoI-XbaI fragment from pMT636 and the 1.4 kb NcoI-EcoRI fragment from pMT636. Plasmid pMT636 is described in International Patent application No. PCT/DK88/00138.

pMT636 is an E. coli—[S. cerevisiae shuttle vector containing the Schizosaccharomyces pombe TPI gene (POT) (Russell, P. R., Gene 40 (1985) 125–130), the S. cerevisiae triosephosphate isomerase promoter and terminator, $TPI_p$ and $TPI_T$ (Alber, T., and Kawasaki, G. J. Mol. Appl. Gen. 1 (1982), 419–434).

The ligation mixture was used to transform a competent E. coli strain ($r^-$, $m^+$) selecting for ampicillin resistance. DNA sequencing showed that plasmids from the resulting colonies contained the correct DNA sequence for TFPI-2 correctly fused to the synthetic yeast signal-leader gene.

One plasmid pKFN-1605 was selected for further use. The construction of plasmid pKFN-1605 is illustrated in FIG. 1.

The expression cassette of plasmid pKFN-1605 contains the following sequence:

$TPI_p$—KFN1000 signal-leader—TFPI2 - $TPI_T$

The DNA sequence of the 412 bp EcoRI-XbaI fragment from pKFN-1605 is shown in SEQ ID No. 11.

Yeast transformation: S. cerevisiae strain MT663 (E2-7B XE11-36 a/α, Δtpi/Δtpi, pep 4-3/pep 4-3) was grown on YPGaL (1% Bacto yeast extract, 2% Bacto peptone, 2% galactose, 1% lactate) to an O.D. at 600 nm of 0.6.

100 ml of culture was harvested by centrifugation, washed with 10 ml of water, recentrifugated and resuspended in 10 ml of a solution containing 1.2M sorbitol, 25 mM $Na_2EDTA$ pH=8.0 and 6.7 mg/ml dithiothreitol. The suspension was incubated at 30° C. for 15 minutes, centrifuged and the cells resuspended in 10 ml of a solution containing 1.2M sorbitol, 10 mM $Na_2EDTA$, 0.1M sodium citrate, pH=5.8, and 2 mg Novozym® 234. The suspension was incubated at 30° C. for 30 minutes, the cells collected by centrifugation, washed in 10 ml of 1.2M sorbitol and 10 ml of CAS (1.2M sorbitol,10 mM $CaCl_2$, 10 mM Tris HCl (Tris=Tris(hydroxymethyl)aminomethane pH=7.5) and resuspended in 2 ml of CAS. For transformation, 0.1 ml of CAS-resuspended cells were mixed with approx. 1 µg of plasmid pKFN-1605 and left at room temperature for 15 minutes. 1 ml of (20% polyethylene glycol 4000, 20 mM $CaCl_2$, 10 mM $CaCl_2$, 10 mM Tris HCl, pH=7.5) was added and the mixture left for a further 30 minutes at room temperature. The mixture was centrifuged and the pellet resuspended in 0.1 ml of SOS (1.2M sorbitol, 33% v/v YPD, 6.7 mM $CaCl_2$, 14 µg/ml leucine) and incubated at 30° C. for 2 hours. The suspension was then centrifuged and the pellet resuspended in 0.5 ml of 1.2M sorbitol. Then, 6 ml of top agar (the SC medium of Sherman et al., (Methods in Yeast Genetics, Cold Spring Harbor Laboratory (1982)) containing 1.2M sorbitol plus 2.5% agar) at 52° C. was added and the suspension poured on top of plates containing the same agar-solidified, sorbitol containing medium.

Transformant colonies were picked after 3 days at 30° C., reisolated and used to start liquid cultures. One such transformant KFN-1593 was selected for further characterization.

Fermentation: Yeast strain KFN-1593 was grown on YPD medium (1% yeast extract, 2% peptone (from Difco Laboratories), and 3% glucose). A 1 liter culture of the strain was shaken at 30° C. to an optical density at 650 nm of 24. After centrifugation the supernatant was isolated.

Purification: The yeast supernatant (1000 ml) adjusted to pH 3.0 with phosphoric acid was applied on a column of S-Sepharose Fast Flow (Pharmacia, 2.6×3.6 cm) equilibrated with 25 mM sodium dihydrogen phosphate, pH=3.5. After wash with equilibration buffer, TFPI-2 assayed as trypsin inhibitory activity was eluted with buffer containing 1M sodium chloride (40 ml). Desalting was obtained on a Sephadex G-25 column (Pharmacia, 2.6×34 cm) equilibrated and eluted with ammonium hydrogen carbonate, pH=7.5. Further purification was performed on a Mono S column (Pharmacia, 0.5×5 cm) by gradient elution over 23 min at 1 ml/min from 0–0.43M sodium chloride in 25 mM sodium dihydrogen phosphate, 10% w/v acetonitrile, pH=3.5. N-glycosylated TFPI-2 and unglycosylated TFPI-2 eluted at 0.20M an 0.26M sodium chloride, respectively. Final purification of unglycosylated TFPI-2 was performed by reverse phase HPLC on a C18 column (Novo Nordisk A/S, 0.4×25 cm) by gradient elution over 30 min at 1 ml/min from 0–50% acetonitrile, 0.1% trifluoroacetic acid.

TFPI-2 eluted at 40% acetonitrile. The purified product was lyophilized and redissolved in water to a concentration of approx. 200 nM. Aliquot samples of this solution were analyzed for amino acid composition (table 1), amino acid sequence, molecular weight (PDMS, found: MW 6840.8, calc.: 6840.6) and protease inhibitory activities.

EXAMPLE 2

Production of [R15K, G16A, Y17R, T19I]-TFPI-2 from Yeast Strain KFN-1811

0.1 µg of the 1.3 kb SphI-BamHI fragment encoding TFPI-2 from plasmid pKFN-1605 was used as a template in two PCR reactions. In the first PCR reaction 100 pmole each of the primers NOR-2022 (GGAGTTTAGTGAACTTGC) and M-460 (GTTATAAAAATACCTGATAATAC-GAGCTTTACATATTCCAGGATC) was used. In the second PCR reaction 100 pmole each of the primers NOR-1495 (TAAGTGGCTCAGAATGA) and M-459 (GATCCTG-GAATATGTAAAGCTCGTATTATCAGG-TATTTTTATAAC) was used.

In the following examples, numbering of the amino acid residue positions refer to positions in the native sequence.

NOR-2022 primes at a position 94 bp downstream of the SphI site. M-460 is complementary to the TFPI-2 DNA-sequence position 263–307, SEQ ID No. 11, except for six mismatches. NOR-1495 primes at a position 561 bp upstream form the BamHI site. M-459 is complementary to M-460.

The PCR reaction was performed in a 100 µl volume using a commercial kit (GeneAmp, Perkin Elmer Cetus) and the following cycle: 95° for 1 min, 50° for 1 min, and 72° for 2 min. After 24 cycles a final cycle was performed in which the 72° step was maintained for 10 min. The PCR products, a 444 bp fragment from the first PCR and a 285 bp fragment from the second, were isolated by electrophoresis on a 2% agarose gel.

Approx. 0.1 µg of each of the two PCR-fragments described above were mixed. A PCR reaction was performed using 100 pmole each of primers NOR-2022 and NOR-1495 and the following cycle: 95° for 1 min, 50° for 2 min, and 72° for 3 min. After 22 cycles a final cycle was performed in which the 72° step was maintained for 10 min.

The resulting 687 bp fragment was purified by electrophoresis on a 1% agarose gel and then digested with EcoRI and XbaI. The resulting 412 bp fragment was ligated to the 9.5 kb NcoI-XbaI fragment from pMT636 and the 1.4 kb NcoI-EcoRI fragment from pMT636. Plasmid pMT636 is described in example 1.

The ligation mixture was used to transform a competent E. coli strain r−, m+) selecting for ampicillin resistance. DNA sequencing showed that plasmids from the resulting colonies contained the correct DNA sequence for [R15K, G16A, Y17R, T19I]-TFPI-2 fused to the synthetic yeast signal-leader gene.

One plasmid pKFN-1798 was selected for further use. The DNA sequence of the 412 bp EcoRI-XbaI fragment from pKFN-1798 is shown in SEQ ID No. 13.

Plasmid pKFN-1798 was transformed in yeast strain MT663 as described in example 1 resulting in yeast strain KFN-1811.

Culturing of the transformed strain KFN-1811 in YPD-medium, analysis for [R15K, G16A, Y17R, T19I]-TFPI-2 in the supernatant, and purification was performed as described in example 1.

EXAMPLE 3

Inhibition of Serine Proteinases by TFPI (domain II) KFN 1593

KFN 1593 was purified from yeast culture medium as described in example 1. The concentration of KFN 1593 was determined using 1% $E_{280\ nm}$=8.3 and $M_w$=6500. Porcine trypsin was from Novo Nordisk (Bagsværd, Denmark), bovine chymotrypsin (TLCK treated) and porcine pancreatic kallikrein was from Sigma Chemical Co (St. Louis, Mo., U.S.A.), human plasmin and human plasma kallikrein was from Kabi (Stockholm, Sweden).

Human neutrophil elastase and cathepsin G was purified from extracts of PMNs according to the method described by Baugh and Travis (Biochemistry 15 (1976) 836–843). Peptidyl nitroanilide substrates, S2251, S2586, S2266, S2302 were from Kabi (Stockholm, Sweden). M4765 and S7388 was from Sigma Chemical Co (St. Louis, Mo., U.S.A.) and FXa-1 was from NycoMed (Oslo, Norway).

Figure 2:
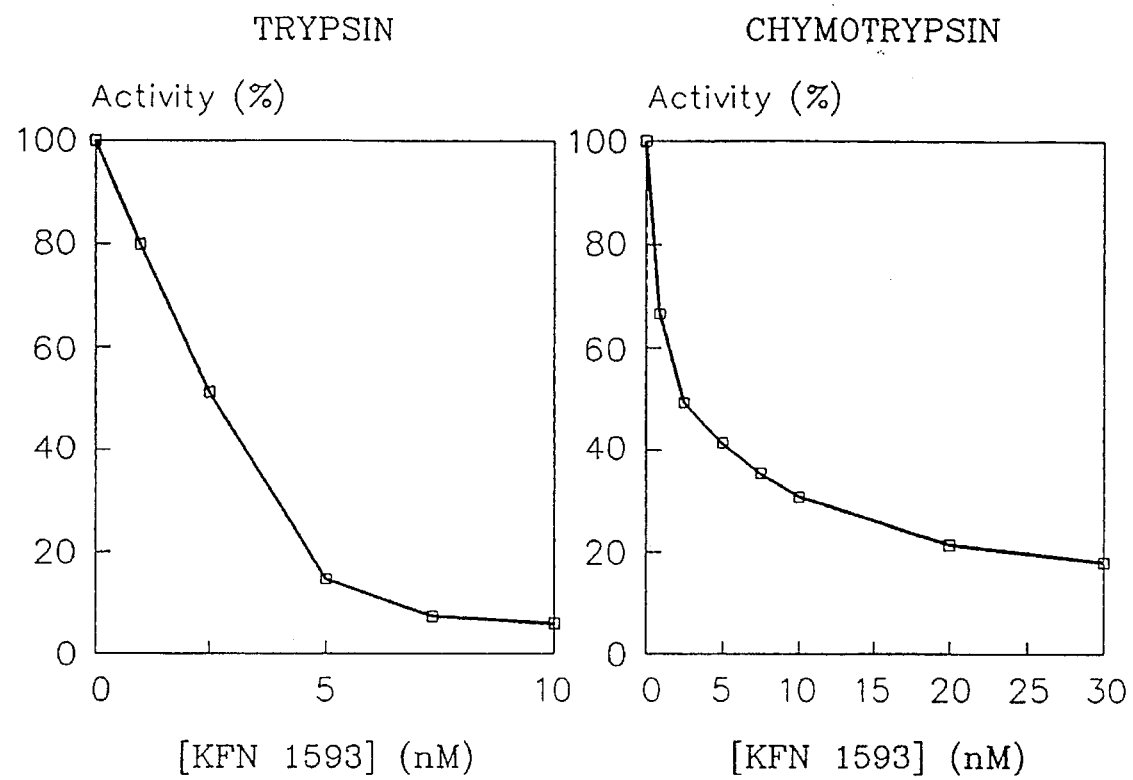
FIG. 2 shows graphs of proteinase activity of trypsin, chymotrypsin, plasmin and Factor Xa vs. concentration of the Kunitz-type protease inhibitor KPN 1593.
Figure 2:
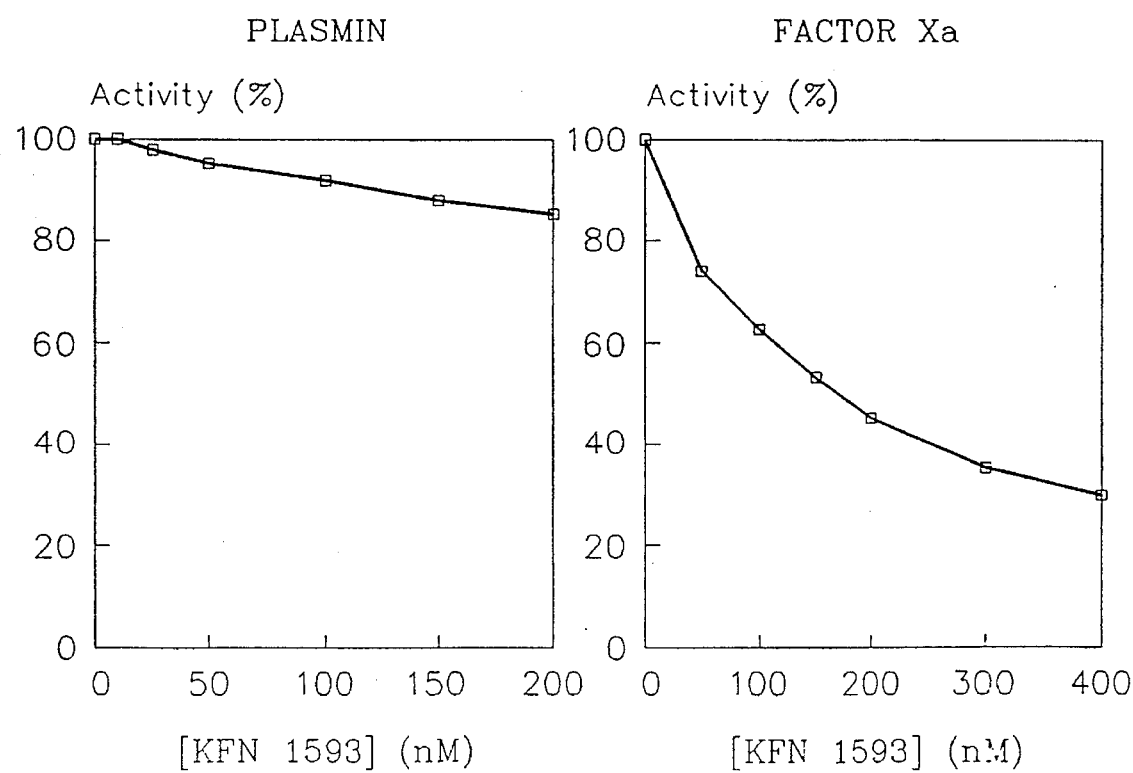
Figure 3:
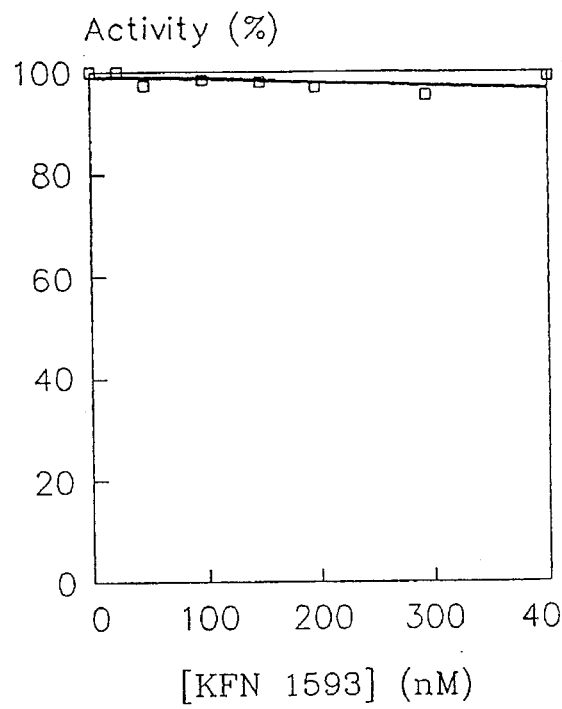
FIG. 3 shows graphs of proteinase activity of glandular kallikrein, plasma kallikrein, cathepsin G and neutrophil elastase vs. concentration of the Kunitz-type protease inhibitor KFN 1593.
Figure 3:
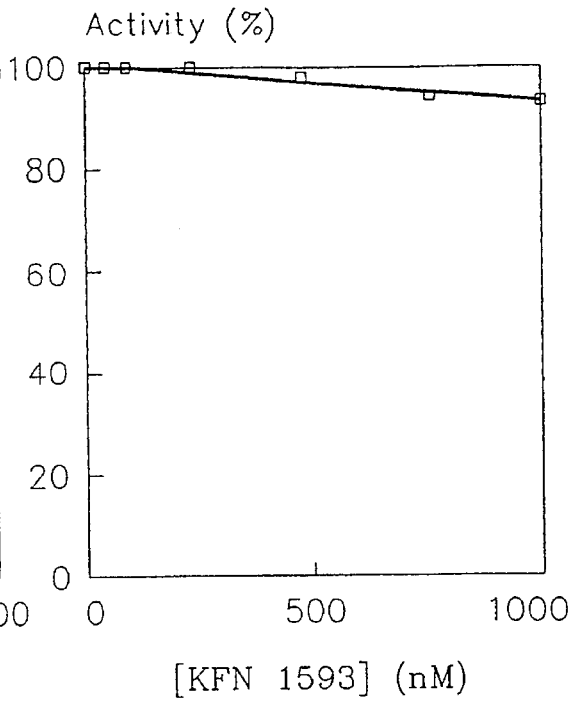
Figure 3:
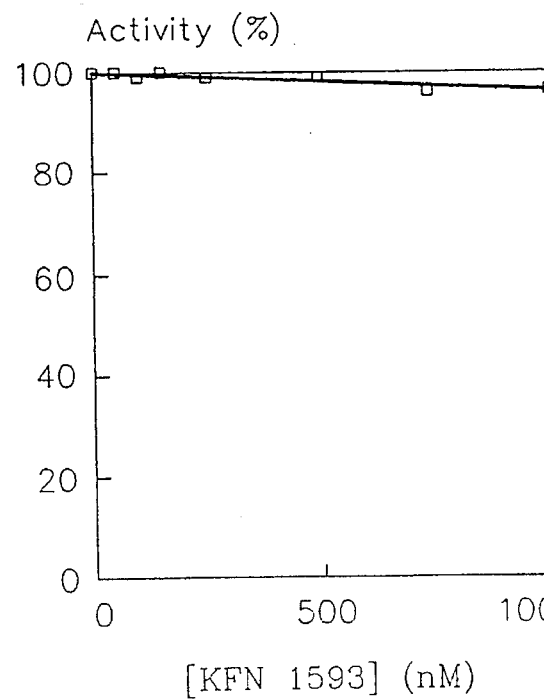
Figure 3:
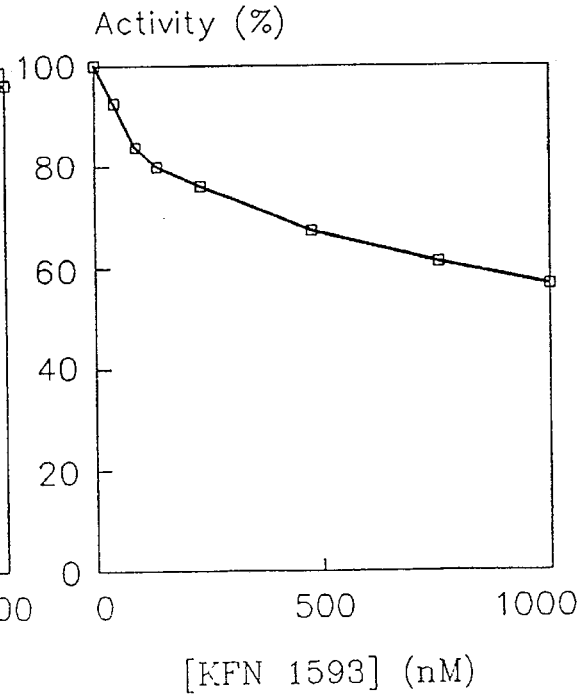

Serine proteinases were incubated with various concentrations of KFN 1593 for 30 min. Substrate was then added and residual proteinase activity was measured at 405 nm. The results are shown in FIG. 2 and FIG. 3.

Unmodified TFPI Kunitz domain II (KFN 1593) is an inhibitor of trypsin ($K_i \cong 5 \times 10^{-9}$M) and factor X. ($K_i$=150 nM). KFN 1593 shows a moderate inhibition of plasmin and neutrophil elastase, whereas the inhibition of Cathepsin G and kallikreins is essentially absent.

TABLE 1

| Amino acid | TFPI-2 | |
|---|---|---|
| | Theor. | Found |
| Ala | 0 | 0.31 |
| Cys | 6 | 5.14 |
| Asx | 9 | 8.94 |
| Glx | 9 | 9.25 |
| Phe | 5 | 4.89 |
| Gly | 6 | 6.01 |
| His | 0 | 0.13 |
| Ile | 3 | 2.82 |
| Lys | 4 | 4.12 |

TABLE 1-continued

| | TFPI-2 | |
|---|---|---|
| Amino acid | Theor. | Found |
| Leu | 3 | 3.04 |
| Met | 1 | 0.82 |
| Pro | 2 | 2.08 |
| Arg | 3 | 2.86 |
| Ser | 0 | 0.17 |
| Thr | 3 | 2.92 |
| Val | 0 | 0.16 |
| Trp | 0 | — |
| Tyr | 4 | 3.75 |
| Total | 58 | 57.41 |

EXAMPLE 4

Production of [R15K, G16A, Y17R, T19I, L39R]-TFPI-2 from Yeast Strain KFN-1867

0.1 μg of the 1.3 kb SphI-BamHI fragment encoding R15K, G16A, Y17R, T19I]-TFPI-2 from plasmid pKFN-1798 was used as a template in two PCR reactions. In the first PCR reaction 100 pmole each of the primers NOR-2022 (GGAGTTTAGTGAACTTGC) and M-462 (CCAGTGTCTCAAAATTGTTCATATTGCCCCTGCATCCACC) was used. In the second PCR reaction 100 pmole each of the primers NOR-1495 (TAAGTGGCTCAGAATGA) and M-461 (GGTGGATGCAGGGGCAATATGAACAATTTTGAGACACTGG) was used.

NOR-2022 primes at a position 94 bp downstream of the SphI site. M-462 is complementary to the TFPI-2 DNA-sequence position 341–380, SEQ ID No. 11, except for two mismatches. NOR-1495 primes at a position 561 bp upstream from the BamHI site. M-461 is complementary to M-462.

The PCR reaction was performed in a 100μl volume using a commercial kit (GeneAmp, Perkin Elmer Cetus) and the following cycle: 95° for 1 min, 50° for 1 min, and 72° for 2 min. After 24 cycles a final cycle was performed in which the 72° step was maintained for 10 min. The PCR products, a 518 bp fragment from the first PCR and a 209 bp fragment from the second, were isolated by electrophoresis on a 2% agarose gel.

Approx. 0.1 μg of each of the two PCR-fragments described above were mixed. A PCR reaction was performed using 100 pmole each of primers NOR-2022 and NOR-1495 and the following cycle: 95° for 1 min, 50° for 2 min, and 72° for 3 min. After 22 cycles a final cycle was performed in which the 72° step was maintained for 10 min.

The resulting 687 bp fragment was purified by electrophoresis on a 1% agarose gel and then digested with EcoRI and XbaI. The resulting 412 bp fragment was ligated to the 9.5 kb NcoI-XbaI fragment from pMT636 and the 1.4 kb NcoI-EcoRI fragment from pMT636. Plasmid pMT636 is described in example 1.

The ligation mixture was used to transform a competent E. coli strain r⁻, m⁺) selecting for ampicillin resistance. DNA sequencing showed that plasmids from the resulting colonies contained the correct DNA sequence for [R15K, G16A, Y17R, T19I, L39R]-TFPI-2 fused to the synthetic yeast signal-leader gene.

One plasmid pKFN-1861 was selected for further use. The DNA sequence of the 412 bp EcoRI-XbaI fragment from pKFN-1861 is shown in SEQ ID No. 15.

Plasmid pKFN-1861 was transformed in yeast strain MT663 as described in example 1 resulting in yeast strain KFN-1867.

Culturing of the transformed strain KFN-1867 in YPD-medium, analysis for [R15K, G16A, Y17R, T19I, L39R]-TFPI-2 in the supernatant, and purification was performed as described in example 1.

EXAMPLE 5

Production of [R15K, G16A, Y17R, T19I, L39R, E46K]-TFPI-2 from Yeast Strain KFN-1868

0.1 μg of the 1.3 kb SphI-BamHI fragment encoding [R15K, G16A, Y17R, T19I]-TFPI-2 from plasmid pKFN-1798 was used as a template in two PCR reactions. In the first PCR reaction 100 pmole each of the primers NOR-2022 (GGAGTTTAGTGAACTTGC) and M-464 (CCAGTGTCTTAAAATTGTTCATATTGCCCCTGCATCCACC) was used. In the second PCR reaction 100 pmole each of the primers NOR-1495 (TAAGTGGCTCAGAATGA) and M-463 (GGTGGATGCAGGGGCAATATGAACAATTTTAAGACACTGG) was used.

NOR-2022 primes at a position 94 bp downstream of the SphI site. M-464 is complementary to the TFPI-2 DNA-sequence position 341–380, SEQ ID No. 11, except for three mismatches. NOR-1495 primes at a position 561 bp upstream from the BamHI site. M-463 is complementary to M-464.

The PCR reaction was performed in a 100μl volume using a commercial kit (GeneAmp, Perkin Elmer Cetus) and the following cycle: 95° for 1 min, 50° for 1 min, and 72° for 2 min. After 24 cycles a final cycle was performed in which the 72° step was maintained for 10 min. The PCR products, a 518 bp fragment from the first PCR and a 209 bp fragment from the second, were isolated by electrophoresis on a 2% agarose gel.

Approx. 0.1 μg of each of the two PCR-fragments described above were mixed. A PCR reaction was performed using 100 pmole each of primers NOR-2022 and NOR-1495 and the following cycle: 95° for 1 min, 50° for 2 min, and 72° for 3 min. After 22 cycles a final cycle was performed in which the 72° step was maintained for 10 min.

The resulting 687 bp fragment was purified by electrophoresis on a 1% agarose gel and then digested with EcoRI and XbaI. The resulting 412 bp fragment was ligated to the 9.5 kb NcoI-XbaI fragment from pMT636 and the 1.4 kb NcoI-EcoRI fragment from pMT636. Plasmid pMT636 is described in example 1.

The ligation mixture was used to transform a competent E. coli strain r⁻, m⁺) selecting for ampicillin resistance. DNA sequencing showed that plasmids from the resulting colonies contained the correct DNA sequence for [R15K, G16A, Y17R, T19I, L39R, E46K]-TFPI-2 fused to the synthetic yeast signal-leader gene.

One plasmid pKFN-1862 was selected for further use. The DNA sequence of the 412 bp EcoRI-XbaI fragment from pKFN-1862 is shown in SEQ ID No. 17.

Plasmid pKFN-1862 was transformed in yeast strain MT663 as described in example 1 resulting in yeast strain KFN-1868.

Culturing of the transformed strain KFN-1868 in YPD-medium, analysis for [R15K, G16A, Y17R, T19I, L39R, E46K]TFPI-2 in the supernatant, and purification was performed as described in example 1.

EXAMPLE 6

Multiple Mutation of TFPI-2 in Position 15 and 16

0.1 μg of the 1.3 kb SphI-BamHI fragment encoding TFPI-2 from plasmid pKFN-1605 was used as a template in two PCR reactions. In the first PCR reaction 100 pmole each of the primers NOR-2022 (GGAGTTTAGTGAACTTGC) and M-749 (AATACCTGGTAATATAA(C/G)C(C/G)A(A/C)ACATATTCCAGGATC) was used. In the second PCR reaction 100 pmole each of the primers NOR-1495 (TAAGTGGCTCAGAATGA) and M-750 (GATCCTGGAATATGT(T/G)T(C/G)G(C/G)TTATATTACCAGGTATT) was used.

NOR-2022 primes at a position 94 bp downstream of the SphI site. M-749 is complementary to the TFPI-2 DNA-sequence position 263–299, SEQ ID No. 11, except for four mismatches. NOR-1495 primes at a position 561 bp upstream from the BamHI site. M-750 is complementary to M-749.

The PCR reaction was performed in a 100 μl volume using a commercial kit (GeneAmp, Perkin Elmer Cetus) and the following cycle: 95° for 1 min, 50° for 1 min, and 72° for 2 min. After 24 cycles a final cycle was performed in which the 72° step was maintained for 10 min. The PCR products, a 439 bp fragment from the first PCR and a 285 bp fragment from the second, were isolated by electrophoresis on a 2% agarose gel. Approx. 0.1 μg of each of the two PCR-fragments described above were mixed. A PCR reaction was performed using 100 pmole each of primers NOR-2022 and NOR-1495 and the following cycle: 95° for 1 min, 50° for 2 min, and 72° for 3 min. After 22 cycles a final cycle was performed in which the 72° step was maintained for 10 min. The resulting 687 bp fragment was purified by electrophoresis on a 1% agarose gel and then digested with EcoRI and XbaI. The resulting 412 bp fragment was ligated to the 2.8 kb EcoRI-XbaI fragment from plasmid pTZ19R (Mead, D. A., Szczesna-Skopura, E., and Kemper, B. Prot. Engin. 1 (1986) 67–74).

The ligation mixture was used to transform a competent E. coli strain r⁻, m⁺ selecting for ampicillin resistance. By DNA sequencing the following six plasmids encoding the indicated TFPI-2 analogs fused to the synthetic yeast signal-leader gene were identified:

| Plasmid | Analog |
| --- | --- |
| pKFN-1885 | [R15F]-TFPI-2 |
| pKFN-1883 | [R15F, G16A]-TFPI-2 |
| pKFN-1905 | [R15L]-TFPI-2 |
| pKFN-1882 | [R15L, G16A]-TFPI-2 |
| pKFN-1887 | [R15V]-TFPI-2 |
| pKFN-1886 | [R15V, G16A]-TFPI-2 |

The 412 bp EcoRI-XbaI fragments from these plasmids were used for the construction of the expression plasmids as described in example 1.

Transformation of yeast strain MT-663 as described in example 1 resulted in the following yeast strains:

| Yeast strain | Analog |
| --- | --- |
| KFN-1896 | [R15F]-TFPI-2 |
| KFN-1894 | [R15F, G16A]-TFPI-2 |
| KFN-1928 | [R15L]-TFPI-2 |
| KFN-1893 | [R15L, G16A]-TFPI-2 |
| KFN-1898 | [R15V]-TFPI-2 |
| KFN-1897 | [R15V, G16A]-TFPI-2 |

Culturing of the transformed yeast strains in YPD-medium, analysis for TFPI-2 analogs in the supernatant, and purification was performed as described in example 1.

EXAMPLE 8

Inhibition of Serine Proteinases by TFPI (domain II) KFN 1811 1867 and 1868

The three TFPI (domain II) variants were purified from yeast culture medium. Their concentrations were determined from the absorbance at 214 nm using BPTI as a standard. The final concentration was determined by titration with trypsin. Porcine trypsin and human recombinant proteins, factor VIIa, activated protein C (ACP), and tPA were obtained from Novo Nordisk A/S (Bagsvaerd, Denmark), so was human thrombin. Bovine chymotrypsin and glandular kallikrein were obtained from Sigma Chemical Co. (St. Louis, Mo., U.S.A.). Truncated human recombinant tissue factor was obtained from Corvas (San Diego, Calif., U.S.A.). Human neutrophil cathepsin G was purified from extracts of PMNs according to the method described by Baugh and Travis (Biochemistry 15 (1976) 836–843). Human plasmin was from Kabi (Stockholm, Sweden), uPA was from Serono (Milan, Italy), human factor Xa was a gift from Dr. W. Kisiel (Albuquerque, N.M., U.S.A.), and human plasma kallikrein was a gift from Dr. I Schousboe (Copenhagen, Denmark).

Peptidyl nitroanilide substrates, S2251, S2302, S2266, S2586, S2288, S2444, S2366, and S2238 were from Kabi (Stockholm, Sweden). S7388 and M4765 were from Sigma Chemical Co. (St. Louis, Mo., U.S.A.) and FXa-1 was from Nycomed (Oslo, Norway).

Serine proteinases were incubated with various concentrations of Kunitz Domain variant for 30 min. Substrate (0.6 mM) was then added and residual proteinase activity was measured at 405 nm. The results are shown in Table 1.

The three variants are strong specific plasmin inhibitors without significant inhibition of other proteinases from plasma tested.

TABLE 1

| | | | Apparent $K_i$ (nM) | | |
| --- | --- | --- | --- | --- | --- |
| Enzyme | Enzyme Conc. | Substrate | KFN 1811 | KFN 1867 | KFN 1868 |
| Trypsin | 10 nM | S2251 | <<1 | <<1 | <<1 |
| Plasmin | 4 nM | S2251 | 3 | 3 | 3 |
| N. elastase | 10 nM | M4765 | n.i. | n.i. | n.i. |
| N. cathepsin G | 50 nM | S7388 | n.i. | n.i. | n.i. |

TABLE 1-continued

| Enzyme | Enzyme Conc. | Substrate | Apparent $K_i$ (nM) | | |
|---|---|---|---|---|---|
| | | | KFN 1811 | KFN 1867 | KFN 1868 |
| Pl. kallikrein | 3 nM | S2302 | >100 | >100 | >100 |
| Gl. kallikrein | 1 U/ml | S2266 | >100 | >100 | >100 |
| chymotrypsin | 2.5 nM | S2586 | 10 | 20 | 20 |
| tPA | 10 nM | S2288 | n.i. | n.i. | n.i. |
| Factor VIIa/TF | 10 nM/15 nM | FXa-1 | n.i. | n.i. | n.i. |
| Factor Xa | 3 nM | FXa-1 | n.i. | n.i. | n.i. |
| uPA | 5 nM | S2444 | n.i. | n.i. | n.i. |
| APC | 5 nM | S2366 | n.i. | n.i. | n.i. |
| Thrombin | 3 NIHu/ml | S2238 | n.i. | n.i. | n.i. |

EXAMPLE 9

Inhibition of Serine Proteinases by TFPI (domain II) KFN 1893, 1897, 1898 and 1928

The four variants were purified from yeast culture medium. Their concentrations were determined from the absorbance at 214 nm using BTPI as a standard. Porcine trypsin was obtained from Novo Nordisk A/S (Bagsvaerd, Denmark), bovine chymotrypsin (TLCK treated) was obtained from Sigma Chemical Co. (St. Louis, Mo., U.S.A.). Truncated human recombinant tissue factor was obtained from Corvas (San Diego, Calif., U.S.A.). Human plasmin was from Kabi (Stockholm, Sweden). Human neutrophil cathepsin G and elastase were purified from extracts of PMNs according to the method described by Baugh and Travis (Biochemistry 15 (1976) 836–843).

Peptidyl nitroanilide substrates, S2251, S2586 were from Kabi (Stockholm, Sweden). S7388 and M4765 were from Sigma Chemical Co. (St. Louis, Mo., U.S.A.).

Serine proteinases were incubated with various concentrations of the variants for 30 min. Substrate (0.6 nM) was then added and residual proteinase activity was measured at 405 nm. The results are shown in Table 2.

The four TFPI Kunitz domain II variants (KFN 1893, 1897, 1898, 1928) were found to be strong inhibitors of neutrophil elastase.

TABLE 2

| Enzyme | Enzyme Conc. | Substrate | Apparent $K_i$ (nM) | | | |
|---|---|---|---|---|---|---|
| | | | KNN 1893 | KFN 1897 | KFN 1898 | KFN 1928 |
| Trypsin | 10 nM | S2251 | n.i. | n.i. | n.i. | n.i. |
| Chymotrypsin | 2.5 nM | S2586 | <5 | w.i. | w.i. | <5 |
| N. elastase | 4 nM | M4765 | 0.23 | 0.46 | 0.35 | 2.2 |
| N. cathepsin G | 50 nM | S7388 | n.i. | n.i. | n.i. | n.i. |
| Plasmin | 4 nM | S2251 | n.i. | n.i. | n.i. | n.i. | n.i. No inhibition at conc. <1 µM; w.i. weak inhibition at 100 nM.

What is claimed is:

1. A variant of human Kunitz-type protease inhibitor domain II of tissue factor pathway inhibitor (TFPI), the variant comprising the following amino acid sequence:

Xaa Xaa Xaa Xaa Xaa Asp Phe Cys Phe Leu Glu Glu Asp Xaa
1           5                        10

Gly Xaa Cys Xaa Xaa Xaa Xaa Xaa Xaa Tyr Phe Tyr Asn Asn
15              20                      25

Gln Thr Lys Gln Cys Glu Arg Phe Xaa Tyr Gly Gly Cys Xaa
    30              35                      40

Xaa Xaa Met Asn Asn Phe Xaa Thr Leu Glu Glu Cys Lys Asn
        45              50                      55

Ile Cys Glu Asp Xaa Xaa Xaa Xaa Xaa (SEQ ID NO:1)
            60              65 wherein
Xaa at position 1 is Lys;
Xaa at position 2 is Pro;
Xaa at position 3 is absent;
Xaa at position 4 is absent;
Xaa at position 5 is absent;
Xaa at position 14 is Pro,
Xaa at position 16 is Ile;
Xaa at position 18 is Lys, Arg, Val, Thr, Leu, Phe, Trp, or Tyr;
Xaa at position 19 is Ala or Gly;
Xaa at position 20 is Arg, Lys, or Tyr;
Xaa at position 21 is Ile;
Xaa at position 22 is Ile, Thr, or Leu;
Xaa at position 23 is Arg;
Xaa at position 37 is Ile, Lys, Thr, Leu, or Val;
Xaa at position 42 is Arg or Lys;
Xaa at position 43 is Gly;
Xaa at position 44 is Asn;
Xaa at position 49 is Asp, Glu, Gln, Asn, Arg, or Lys;
Xaa at position 61 is absent;
Xaa at position 62 is absent;
Xaa at position 63 is absent;
Xaa at position 64 is absent; and Xaa at position 65 is Gly;
with the proviso that at least one of the amino acid residues designated Xaa is different from the amino acid residue of the native sequence, and wherein the variant has serine protease inhibitory activity.

2. A variant according to claim 1, which has the following amino acid sequence

Lys Pro Asp Phe Cys Phe Leu Glu Glu Asp Pro Gly Ile Cys Lys Ala Arg Ile Thr Arg Tyr Phe Tyr Asn Asn Gln Thr Lys Gln Cys Glu Arg Phe Lys Tyr Gly Gly Cys Leu Gly Asn Met Asn Asn Phe Glu Thr Leu Glu Glu Cys Lys Asn Ile Cys Glu Asp Gly (SEQ ID No. 3).

3. A variant according to claim 1, which has the following amino acid sequence

Lys Pro Asp Phe Cys Phe Leu Glu Glu Asp Pro Gly Ile Cys Lys Ala Arg Ile Thr Arg Tyr Phe Tyr Asn Asn Gln Thr Lys Gln Cys Glu Arg Phe Lys Tyr Gly Gly Cys Arg Gly Asn Met Asn Asn Phe Glu Thr Leu Glu Glu Cys Lys Asn Ile Cys Glu Asp Gly (SEQ ID No. 4).

4. A variant according to claim 1, which has the following amino acid sequence

Lys Pro Asp Phe Cys Phe Leu Glu Glu Asp Pro Gly Ile Cys Lys Ala Arg Ile Thr Arg Tyr Phe Tyr Asn Asn Gln Thr Lys Gln Cys Glu Arg Phe Lys Tyr Gly Gly Cys Arg Gly Asn Met Asn Asn Phe Lys Thr Leu Glu Glu Cys Lys Asn Ile Cys Glu Asp Gly (SEQ ID No. 5).

5. A variant according to claim 1 comprising the following amino acid sequence

Lys Pro Asp Phe Cys Phe Leu Glu Glu Asp Pro Gly Pro Cys Lys Ala Arg Ile Ile Arg Tyr Phe Tyr Asn Asn Gln Thr Lys Gln Cys Glu Arg Phe Val Tyr Gly Gly Cys Arg Ala Lys Met Asn Asn Phe Lys Thr Leu Glu Glu Cys Lys Asn Ile Cys Glu Asp Gly (SEQ ID No. 6).

6. A DNA construct comprising a DNA sequence encoding a human Kunitz-type protease inhibitor variant according to claim 1.

7. A recombinant expression vector comprising a DNA construct according to claim 6.

8. A cell containing a DNA construct according to claim 6.

9. A cell containing an expression vector according to claim 7.

10. A method of producing a human Kunitz-type protease inhibitor variant according to claim 1, the method comprising culturing a cell according to claim 8 under conditions conducive to the expression of the protein, and recovering the resulting protein from the culture.

11. A method of producing a human Kunitz-type protease inhibitor variant according to claim 1, the method comprising culturing a cell according to claim 9 under conditions conducive to the expression of the protein, and recovering the resulting protein from the culture.

12. A variant according to claim 1 which inhibits at least one of the proteases selected from the group consisting of chymotrypsin, trypsin, plasmin, cathepsin G, plasma kallikrein, glandular kallikrein and elastase.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Xaa Xaa Xaa Xaa Xaa Asp Phe Cys Phe Leu Glu Glu Asp Xaa Gly Xaa
 1               5                  10                  15
Cys Xaa Xaa Xaa Xaa Xaa Xaa Tyr Phe Tyr Asn Asn Gln Thr Lys Gln
                20                  25                  30
Cys Glu Arg Phe Xaa Tyr Gly Gly Cys Xaa Xaa Xaa Met Asn Asn Phe
                35                  40                  45
Xaa Thr Leu Glu Glu Cys Lys Asn Ile Cys Glu Asp Xaa Xaa Xaa Xaa
    50                  55                  60
```

```
           Xaa
           65
```

( 2 ) INFORMATION FOR SEQ ID NO: 2:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO: 2:

```
Xaa  Xaa  Xaa  Xaa  Xaa  Asp  Phe  Cys  Phe  Leu  Glu  Glu  Asp  Xaa  Gly  Xaa
1                  5                             10                            15

Cys  Xaa  Xaa  Xaa  Xaa  Xaa  Xaa  Tyr  Phe  Tyr  Asn  Xaa  Gln  Xaa  Lys  Gln
              20                        25                        30

Cys  Glu  Arg  Phe  Xaa  Tyr  Gly  Gly  Cys  Xaa  Xaa  Xaa  Met  Asn  Asn  Phe
          35                       40                        45

Xaa  Thr  Leu  Glu  Glu  Cys  Lys  Asn  Ile  Cys  Glu  Asp  Xaa  Xaa  Xaa  Xaa
     50                       55                        60

Xaa
65
```

( 2 ) INFORMATION FOR SEQ ID NO: 3:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO: 3:

```
Lys  Pro  Asp  Phe  Cys  Phe  Leu  Glu  Glu  Asp  Pro  Gly  Ile  Cys  Lys  Ala
1                  5                             10                            15

Arg  Ile  Thr  Arg  Tyr  Phe  Tyr  Asn  Asn  Gln  Thr  Lys  Gln  Cys  Glu  Arg
              20                        25                        30

Phe  Lys  Tyr  Gly  Gly  Cys  Leu  Gly  Asn  Met  Asn  Asn  Phe  Glu  Thr  Leu
          35                       40                        45

Glu  Glu  Cys  Lys  Asn  Ile  Cys  Glu  Asp  Gly
     50                       55
```

( 2 ) INFORMATION FOR SEQ ID NO: 4:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO: 4:

```
Lys  Pro  Asp  Phe  Cys  Phe  Leu  Glu  Glu  Asp  Pro  Gly  Ile  Cys  Lys  Ala
1                  5                             10                            15

Arg  Ile  Thr  Arg  Tyr  Phe  Tyr  Asn  Asn  Gln  Thr  Lys  Gln  Cys  Glu  Arg
```

```
                        20                      25                      30
    Phe  Lys  Tyr  Gly  Gly  Cys  Arg  Gly  Asn  Met  Asn  Asn  Phe  Glu  Thr  Leu
              35                      40                      45

Glu  Glu  Cys  Lys  Asn  Ile  Cys  Glu  Asp  Gly
         50                      55
```

( 2 ) INFORMATION FOR SEQ ID NO: 5:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO: 5:

```
    Lys  Pro  Asp  Phe  Cys  Phe  Leu  Glu  Glu  Asp  Pro  Gly  Ile  Cys  Lys  Ala
    1                   5                        10                      15

Arg  Ile  Thr  Arg  Tyr  Phe  Tyr  Asn  Asn  Gln  Thr  Lys  Gln  Cys  Glu  Arg
                   20                      25                      30

Phe  Lys  Tyr  Gly  Gly  Cys  Arg  Gly  Asn  Met  Asn  Asn  Phe  Lys  Thr  Leu
              35                      40                      45

Glu  Glu  Cys  Lys  Asn  Ile  Cys  Glu  Asp  Gly
         50                      55
```

( 2 ) INFORMATION FOR SEQ ID NO: 6:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO: 6:

```
    Lys  Pro  Asp  Phe  Cys  Phe  Leu  Glu  Glu  Asp  Pro  Gly  Pro  Cys  Lys  Ala
    1                   5                        10                      15

Arg  Ile  Ile  Arg  Tyr  Phe  Tyr  Asn  Asn  Gln  Thr  Lys  Gln  Cys  Glu  Arg
                   20                      25                      30

Phe  Val  Tyr  Gly  Gly  Cys  Arg  Ala  Lys  Met  Asn  Asn  Phe  Lys  Thr  Leu
              35                      40                      45

Glu  Glu  Cys  Lys  Asn  Ile  Cys  Glu  Asp  Gly
         50                      55
```

( 2 ) INFORMATION FOR SEQ ID NO: 7:

( i ) SEQUENCE CHARACTERISTICS:
        ( A ) LENGTH: 945 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: CDS
        ( B ) LOCATION: 365..538

( x i ) SEQUENCE DESCRIPTION: SEQ ID NO: 7:

```
GGATCCGAAT  TCCACCATGA  AGAAAGTACA  TGCACTTTGG  GCTTCTGTAT  GCCTGCTGCT          60

TAATCTTGCC  CCTGCCCCTC  TTAATGCTGA  TTCTGAGGAA  GATGAAGAAC  ACACAATTAT         120

CACAGATACG  GAGTTGCCAC  CACTGAAACT  TATGCATTCA  TTTTGTGCAT  TCAAGGCGGA         180

TGATGGCCCA  TGTAAAGCAA  TCATGAAAAG  ATTTTTCTTC  AATATTTTCA  CTCGACAGTG         240

CGAAGAATTT  ATATATGGGG  GATGTGAAGG  AAATCAGAAT  CGATTTGAAA  GTCTGGAAGA         300

GTGCAAAAAA  ATGTGTACAA  GAGATAATGC  AAACAGGATT  ATAAAGACAA  CATTGCAACA         360
```

```
AGAA AAG CCA GAT TTC TGC TTT TTG GAA GAA GAT CCT GGA ATA TGT CGA              409
     Lys Pro Asp Phe Cys Phe Leu Glu Glu Asp Pro Gly Ile Cys Arg
     1               5                   10                  15

GGT TAT ATT ACC AGG TAT TTT TAT AAC AAT CAG ACA AAA CAG TGT GAA              457
Gly Tyr Ile Thr Arg Tyr Phe Tyr Asn Asn Gln Thr Lys Gln Cys Glu
            20                  25                  30

CGT TTC AAG TAT GGT GGA TGC CTG GGC AAT ATG AAC AAT TTT GAG ACA              505
Arg Phe Lys Tyr Gly Gly Cys Leu Gly Asn Met Asn Asn Phe Glu Thr
        35                  40                  45

CTG GAA GAA TGC AAG AAC ATT TGT GAA GAT GGT CCGAATGGTT TCCAGGTGGA            558
Leu Glu Glu Cys Lys Asn Ile Cys Glu Asp Gly
            50                  55
```

```
TAATTATGGA  ACCCAGCTCA  ATGCTGTGAA  TAACTCCCTG  ACTCCGCAAT  CAACCAAGGT        618

TCCCAGCCTT  TTTGAATTTC  ACGGTCCCTC  ATGGTGTCTC  ACTCCAGCAG  ACAGAGGATT        678

GTGTCGTGCC  AATGAGAACA  GATTCTACTA  CAATTCAGTC  ATTGGGAAAT  GCCGCCCATT        738

TAAGTACAGT  GGATGTGGGG  GAAATGAAAA  CAATTTTACT  TCCAAACAAG  AATGTCTGAG        798

GGCATGTAAA  AAAGGTTTCA  TCCAAAGAAT  ATCAAAAGGA  GGCCTAATTA  AAACCAAAAG        858

AAAAAGAAAG  AAGCAGAGAG  TGAAAATAGC  ATATGAAGAG  ATCTTTGTTA  AAAATATGTG        918

AATTTGTTAT  AGCAATGTAA  CTCTAGA                                                945
```

( 2 ) INFORMATION FOR SEQ ID NO: 8:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

```
Lys Pro Asp Phe Cys Phe Leu Glu Glu Asp Pro Gly Ile Cys Arg Gly
1               5                   10                  15

Tyr Ile Thr Arg Tyr Phe Tyr Asn Asn Gln Thr Lys Gln Cys Glu Arg
            20                  25                  30

Phe Lys Tyr Gly Gly Cys Leu Gly Asn Met Asn Asn Phe Glu Thr Leu
        35                  40                  45

Glu Glu Cys Lys Asn Ile Cys Glu Asp Gly
    50                  55
```

( 2 ) INFORMATION FOR SEQ ID NO: 9:

( i ) SEQUENCE CHARACTERISTICS:
        ( A ) LENGTH: 235 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:

(A) ORGANISM: synthetic (ix) FEATURE:
    (A) NAME/KEY: CDS
    (B) LOCATION: 77..235

(xi) SEQUENCE DESCRIPTION: SEQ ID NO: 9:

```
GAATTCCATT CAAGAATAGT TCAAACAAGA AGATTACAAA CTATCAATTT CATACACAAT         60

ATAAACGACC AAAAGA ATG AAG GCT GTT TTC TTG GTT TTG TCC TTG ATC           109
               Met Lys Ala Val Phe Leu Val Leu Ser Leu Ile
                 1               5                  10

GGA TTC TGC TGG GCC CAA CCA GTC ACT GGC GAT GAA TCA TCT GTT GAG          157
Gly Phe Cys Trp Ala Gln Pro Val Thr Gly Asp Glu Ser Ser Val Glu
             15              20                  25

ATT CCG GAA GAG TCT CTG ATC ATC GCT GAA AAC ACC ACT TTG GCT AAC          205
Ile Pro Glu Glu Ser Leu Ile Ile Ala Glu Asn Thr Thr Leu Ala Asn
         30                  35                  40

GTC GCC ATG GCT GAG AGA TTG GAG AAG AGA                                  235
Val Ala Met Ala Glu Arg Leu Glu Lys Arg
         45                  50
```

(2) INFORMATION FOR SEQ ID NO: 10:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Lys Ala Val Phe Leu Val Leu Ser Leu Ile Gly Phe Cys Trp Ala
  1               5                  10                  15

Gln Pro Val Thr Gly Asp Glu Ser Ser Val Glu Ile Pro Glu Glu Ser
             20                  25                  30

Leu Ile Ile Ala Glu Asn Thr Thr Leu Ala Asn Val Ala Met Ala Glu
         35                  40                  45

Arg Leu Glu Lys Arg
         50
```

(2) INFORMATION FOR SEQ ID NO: 11:

(i) SEQUENCE CHARACTERISTICS:
        (A) LENGTH: 418 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: synthetic/human (ix) FEATURE:
        (A) NAME/KEY: CDS
        (B) LOCATION: 77..409

(ix) FEATURE:
        (A) NAME/KEY: sig_peptide
        (B) LOCATION: 77..235

(ix) FEATURE:
        (A) NAME/KEY: mat_peptide
        (B) LOCATION: 236..409

(xi) SEQUENCE DESCRIPTION: SEQ ID NO: 11:

```
GAATTCCATT CAAGAATAGT TCAAACAAGA AGATTACAAA CTATCAATTT CATACACAAT         60
```

```
ATAAACGACC AAAAGA ATG AAG GCT GTT TTC TTG GTT TTG TCC TTG ATC                              109
               Met Lys Ala Val Phe Leu Val Leu Ser Leu Ile
               -53         -50                     -45

GGA TTC TGC TGG GCC CAA CCA GTC ACT GGC GAT GAA TCA TCT GTT GAG               157
Gly Phe Cys Trp Ala Gln Pro Val Thr Gly Asp Glu Ser Ser Val Glu
        -40             -35                 -30

ATT CCG GAA GAG TCT CTG ATC ATC GCT GAA AAC ACC ACT TTG GCT AAC               205
Ile Pro Glu Glu Ser Leu Ile Ile Ala Glu Asn Thr Thr Leu Ala Asn
    -25             -20                     -15

GTC GCC ATG GCT GAG AGA TTG GAG AAG AGA AAG CCA GAT TTC TGC TTT               253
Val Ala Met Ala Glu Arg Leu Glu Lys Arg Lys Pro Asp Phe Cys Phe
-10                 -5                   1             5

TTG GAA GAA GAT CCT GGA ATA TGT CGA GGT TAT ATT ACC AGG TAT TTT               301
Leu Glu Glu Asp Pro Gly Ile Cys Arg Gly Tyr Ile Thr Arg Tyr Phe
                10              15              20

TAT AAC AAT CAG ACA AAA CAG TGT GAA CGT TTC AAG TAT GGT GGA TGC               349
Tyr Asn Asn Gln Thr Lys Gln Cys Glu Arg Phe Lys Tyr Gly Gly Cys
            25              30              35

CTG GGC AAT ATG AAC AAT TTT GAG ACA CTG GAA GAA TGC AAG AAC ATT               397
Leu Gly Asn Met Asn Asn Phe Glu Thr Leu Glu Glu Cys Lys Asn Ile
    40              45              50

TGT GAA GAT GGT TAATCTAGA                                                     418
Cys Glu Asp Gly
55
```

( 2 ) INFORMATION FOR SEQ ID NO: 12:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 12:

```
Met Lys Ala Val Phe Leu Val Leu Ser Leu Ile Gly Phe Cys Trp Ala
-53         -50                 -45                 -40

Gln Pro Val Thr Gly Asp Glu Ser Ser Val Glu Ile Pro Glu Glu Ser
        -35             -30              -25

Leu Ile Ile Ala Glu Asn Thr Thr Leu Ala Asn Val Ala Met Ala Glu
    -20             -15                  -10

Arg Leu Glu Lys Arg Lys Pro Asp Phe Cys Phe Leu Glu Glu Asp Pro
-5                   1               5                     10

Gly Ile Cys Arg Gly Tyr Ile Thr Arg Tyr Phe Tyr Asn Asn Gln Thr
        15              20                      25

Lys Gln Cys Glu Arg Phe Lys Tyr Gly Gly Cys Leu Gly Asn Met Asn
        30              35                      40

Asn Phe Glu Thr Leu Glu Glu Cys Lys Asn Ile Cys Glu Asp Gly
    45              50                      55
```

( 2 ) INFORMATION FOR SEQ ID NO: 13:

( i ) SEQUENCE CHARACTERISTICS:
        ( A ) LENGTH: 418 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: synthetic ( i x ) FEATURE:

(A) NAME/KEY: CDS
(B) LOCATION: 77..409

(ix) FEATURE:
(A) NAME/KEY: sig_peptide
(B) LOCATION: 77..235

(ix) FEATURE:
(A) NAME/KEY: mat_peptide
(B) LOCATION: 236..409

(xi) SEQUENCE DESCRIPTION: SEQ ID NO: 13:

| | | | | | | |
|---|---|---|---|---|---|---|
| GAATTCCATT | CAAGAATAGT | TCAAACAAGA | AGATTACAAA | CTATCAATTT | CATACACAAT | 60 |

ATAAACGACC AAAAGA ATG AAG GCT GTT TTC TTG GTT TTG TCC TTG ATC    109
              Met Lys Ala Val Phe Leu Val Leu Ser Leu Ile
              -53          -50                       -45

GGA TTC TGC TGG GCC CAA CCA GTC ACT GGC GAT GAA TCA TCT GTT GAG   157
Gly Phe Cys Trp Ala Gln Pro Val Thr Gly Asp Glu Ser Ser Val Glu
        -40              -35                      -30

ATT CCG GAA GAG TCT CTG ATC ATC GCT GAA AAC ACC ACT TTG GCT AAC   205
Ile Pro Glu Glu Ser Leu Ile Ile Ala Glu Asn Thr Thr Leu Ala Asn
    -25                  -20                  -15

GTC GCC ATG GCT GAG AGA TTG GAG AAG AGA AAG CCA GAT TTC TGC TTT   253
Val Ala Met Ala Glu Arg Leu Glu Lys Arg Lys Pro Asp Phe Cys Phe
-10                   -5                    1              5

TTG GAA GAA GAT CCT GGA ATA TGT AAA GCT CGT ATT ATC AGG TAT TTT   301
Leu Glu Glu Asp Pro Gly Ile Cys Lys Ala Arg Ile Ile Arg Tyr Phe
             10              15                       20

TAT AAC AAT CAG ACA AAA CAG TGT GAA CGT TTC AAG TAT GGT GGA TGC   349
Tyr Asn Asn Gln Thr Lys Gln Cys Glu Arg Phe Lys Tyr Gly Gly Cys
         25                 30                  35

CTG GGC AAT ATG AAC AAT TTT GAG ACA CTG GAA GAA TGC AAG AAC ATT   397
Leu Gly Asn Met Asn Asn Phe Glu Thr Leu Glu Glu Cys Lys Asn Ile
        40                  45                  50

TGT GAA GAT GGT TAATCTAGA                                         418
Cys Glu Asp Gly
55

(2) INFORMATION FOR SEQ ID NO: 14:

(i) SEQUENCE CHARACTERISTICS:
(A) LENGTH: 111 amino acids
(B) TYPE: amino acid
(D) TOPOLOGY: linear (ii) MOLECULE TYPE: protein (xi) SEQUENCE DESCRIPTION: SEQ ID NO: 14:

Met Lys Ala Val Phe Leu Val Leu Ser Leu Ile Gly Phe Cys Trp Ala
-53          -50                      -45                  -40

Gln Pro Val Thr Gly Asp Glu Ser Ser Val Glu Ile Pro Glu Glu Ser
        -35              -30                  -25

Leu Ile Ile Ala Glu Asn Thr Thr Leu Ala Asn Val Ala Met Ala Glu
    -20              -15                  -10

Arg Leu Glu Lys Arg Lys Pro Asp Phe Cys Phe Leu Glu Glu Asp Pro
 -5              1               5                        10

Gly Ile Cys Lys Ala Arg Ile Ile Arg Tyr Phe Tyr Asn Asn Gln Thr
             15                  20                   25

Lys Gln Cys Glu Arg Phe Lys Tyr Gly Gly Cys Leu Gly Asn Met Asn
        30                  35                   40

Asn Phe Glu Thr Leu Glu Glu Cys Lys Asn Ile Cys Glu Asp Gly
        45              50                  55

( 2 ) INFORMATION FOR SEQ ID NO: 15:

( i ) SEQUENCE CHARACTERISTICS:
        ( A ) LENGTH: 418 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: synthetic ( i x ) FEATURE:
        ( A ) NAME/KEY: CDS
        ( B ) LOCATION: 77..409

( i x ) FEATURE:
        ( A ) NAME/KEY: sig_peptide
        ( B ) LOCATION: 77..235

( i x ) FEATURE:
        ( A ) NAME/KEY: mat_peptide
        ( B ) LOCATION: 236..409

( x i ) SEQUENCE DESCRIPTION: SEQ ID NO: 15:

```
GAATTCCATT  CAAGAATAGT  TCAAACAAGA  AGATTACAAA  CTATCAATTT  CATACACAAT         60

ATAAACGACC  AAAAGA ATG AAG GCT GTT TTC TTG GTT TTG TCC TTG ATC                109
                   Met Lys Ala Val Phe Leu Val Leu Ser Leu Ile
                   -53         -50                     -45

GGA TTC TGC TGG GCC CAA CCA GTC ACT GGC GAT GAA TCA TCT GTT GAG               157
Gly Phe Cys Trp Ala Gln Pro Val Thr Gly Asp Glu Ser Ser Val Glu
        -40             -35                     -30

ATT CCG GAA GAG TCT CTG ATC ATC GCT GAA AAC ACC ACT TTG GCT AAC               205
Ile Pro Glu Glu Ser Leu Ile Ile Ala Glu Asn Thr Thr Leu Ala Asn
    -25             -20                     -15

GTC GCC ATG GCT GAG AGA TTG GAG AAG AGA AAG CCA GAT TTC TGC TTT               253
Val Ala Met Ala Glu Arg Leu Glu Lys Arg Lys Pro Asp Phe Cys Phe
-10              -5                    1               5

TTG GAA GAA GAT CCT GGA ATA TGT AAA GCT CGT ATT ATC AGG TAT TTT               301
Leu Glu Glu Asp Pro Gly Ile Cys Lys Ala Arg Ile Ile Arg Tyr Phe
             10              15                      20

TAT AAC AAT CAG ACA AAA CAG TGT GAA CGT TTC AAG TAT GGT GGA TGC               349
Tyr Asn Asn Gln Thr Lys Gln Cys Glu Arg Phe Lys Tyr Gly Gly Cys
             25              30                      35

AGG GGC AAT ATG AAC AAT TTT GAG ACA CTG GAA GAA TGC AAG AAC ATT               397
Arg Gly Asn Met Asn Asn Phe Glu Thr Leu Glu Glu Cys Lys Asn Ile
         40              45                      50

TGT GAA GAT GGT TAATCTAGA                                                     418
Cys Glu Asp Gly
55
```

( 2 ) INFORMATION FOR SEQ ID NO: 16:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 16:

```
Met Lys Ala Val Phe Leu Val Leu Ser Leu Ile Gly Phe Cys Trp Ala
-53         -50                     -45                     -40

Gln Pro Val Thr Gly Asp Glu Ser Ser Val Glu Ile Pro Glu Glu Ser
            -35                     -30                 -25
```

```
Leu  Ile  Ile  Ala  Glu  Asn  Thr  Thr  Leu  Ala  Asn  Val  Ala  Met  Ala  Glu
     -20                 -15                      -10

Arg  Leu  Glu  Lys  Arg  Lys  Pro  Asp  Phe  Cys  Phe  Leu  Glu  Glu  Asp  Pro
-5                       1                    5                        10

Gly  Ile  Cys  Lys  Ala  Arg  Ile  Ile  Arg  Tyr  Phe  Tyr  Asn  Asn  Gln  Thr
          15                           20                       25

Lys  Gln  Cys  Glu  Arg  Phe  Lys  Tyr  Gly  Gly  Cys  Arg  Gly  Asn  Met  Asn
          30                      35                      40

Asn  Phe  Glu  Thr  Leu  Glu  Glu  Cys  Lys  Asn  Ile  Cys  Glu  Asp  Gly
     45                      50                      55
```

( 2 ) INFORMATION FOR SEQ ID NO: 17:

( i ) SEQUENCE CHARACTERISTICS:
        ( A ) LENGTH: 418 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: synthetic ( i x ) FEATURE:
        ( A ) NAME/KEY: CDS
        ( B ) LOCATION: 77..409

( i x ) FEATURE:
        ( A ) NAME/KEY: sig_peptide
        ( B ) LOCATION: 77..235

( i x ) FEATURE:
        ( A ) NAME/KEY: mat_peptide
        ( B ) LOCATION: 236..409

( x i ) SEQUENCE DESCRIPTION: SEQ ID NO: 17:

```
GAATTCCATT  CAAGAATAGT  TCAAACAAGA  AGATTACAAA  CTATCAATTT  CATACACAAT         60

ATAAACGACC  AAAAGA ATG  AAG  GCT  GTT  TTC  TTG  GTT  TTG  TCC  TTG  ATC      109
                   Met  Lys  Ala  Val  Phe  Leu  Val  Leu  Ser  Leu  Ile
                   -53            -50                           -45

GGA  TTC  TGC  TGG  GCC  CAA  CCA  GTC  ACT  GGC  GAT  GAA  TCA  TCT  GTT  GAG    157
Gly  Phe  Cys  Trp  Ala  Gln  Pro  Val  Thr  Gly  Asp  Glu  Ser  Ser  Val  Glu
          -40                      -35                           -30

ATT  CCG  GAA  GAG  TCT  CTG  ATC  ATC  GCT  GAA  AAC  ACC  ACT  TTG  GCT  AAC    205
Ile  Pro  Glu  Glu  Ser  Leu  Ile  Ile  Ala  Glu  Asn  Thr  Thr  Leu  Ala  Asn
     -25                      -20                      -15

GTC  GCC  ATG  GCT  GAG  AGA  TTG  GAG  AAG  AGA  AAG  CCA  GAT  TTC  TGC  TTT    253
Val  Ala  Met  Ala  Glu  Arg  Leu  Glu  Lys  Arg  Lys  Pro  Asp  Phe  Cys  Phe
-10                      -5                        1                    5

TTG  GAA  GAA  GAT  CCT  GGA  ATA  TGT  AAA  GCT  CGT  ATT  ATC  AGG  TAT  TTT    301
Leu  Glu  Glu  Asp  Pro  Gly  Ile  Cys  Lys  Ala  Arg  Ile  Ile  Arg  Tyr  Phe
               10                      15                      20

TAT  AAC  AAT  CAG  ACA  AAA  CAG  TGT  GAA  CGT  TTC  AAG  TAT  GGT  GGA  TGC    349
Tyr  Asn  Asn  Gln  Thr  Lys  Gln  Cys  Glu  Arg  Phe  Lys  Tyr  Gly  Gly  Cys
               25                      30                      35

AGG  GGC  AAT  ATG  AAC  AAT  TTT  AAG  ACA  CTG  GAA  GAA  TGC  AAG  AAC  ATT    397
Arg  Gly  Asn  Met  Asn  Asn  Phe  Lys  Thr  Leu  Glu  Glu  Cys  Lys  Asn  Ile
          40                      45                      50

TGT  GAA  GAT  GGT  TAATCTAGA                                                  418
Cys  Glu  Asp  Gly
55
```

( 2 ) INFORMATION FOR SEQ ID NO: 18:

( i ) SEQUENCE CHARACTERISTICS:
    ( A ) LENGTH: 111 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 18:

| Met | Lys | Ala | Val | Phe | Leu | Val | Leu | Ser | Leu | Ile | Gly | Phe | Cys | Trp | Ala |
| -53 |     |     | -50 |     |     |     |     | -45 |     |     |     |     | -40 |     |     |
| Gln | Pro | Val | Thr | Gly | Asp | Glu | Ser | Ser | Val | Glu | Ile | Pro | Glu | Glu | Ser |
|     |     | -35 |     |     |     |     | -30 |     |     |     |     | -25 |     |     |     |
| Leu | Ile | Ile | Ala | Glu | Asn | Thr | Thr | Leu | Ala | Asn | Val | Ala | Met | Ala | Glu |
|     | -20 |     |     |     |     | -15 |     |     |     |     | -10 |     |     |     |     |
| Arg | Leu | Glu | Lys | Arg | Lys | Pro | Asp | Phe | Cys | Phe | Leu | Glu | Glu | Asp | Pro |
| -5  |     |     |     |     | 1   |     |     |     | 5   |     |     |     |     | 10  |     |
| Gly | Ile | Cys | Lys | Ala | Arg | Ile | Ile | Arg | Tyr | Phe | Tyr | Asn | Asn | Gln | Thr |
|     |     |     | 15  |     |     |     |     | 20  |     |     |     |     | 25  |     |     |
| Lys | Gln | Cys | Glu | Arg | Phe | Lys | Tyr | Gly | Gly | Cys | Arg | Gly | Asn | Met | Asn |
|     |     | 30  |     |     |     |     | 35  |     |     |     |     | 40  |     |     |     |
| Asn | Phe | Lys | Thr | Leu | Glu | Glu | Cys | Lys | Asn | Ile | Cys | Glu | Asp | Gly |
|     | 45  |     |     |     |     | 50  |     |     |     |     | 55  |     |     |     |